United States Patent [19]

Leppard et al.

[11] Patent Number: 4,996,326

[45] Date of Patent: Feb. 26, 1991

[54] 2-(2-HYDROXYPHENYL)-BENZOTRIAZOLE DERIVATIVES, SUBSTITUTED BY BRANCHED LONG CHAIN ALKYL GROUPS CONTAINING ESTER MOIETIES

[75] Inventors: David G. Leppard, Marly; Mario Slongo, Taffers; Jean Rody, Riehen, all of Switzerland

[73] Assignee: Ciba-Geigy Corporation, Ardsley, N.Y.

[21] Appl. No.: 464,477

[22] Filed: Jan. 12, 1990

Related U.S. Application Data

[63] Continuation-in-part of Ser. No. 285,680, Dec. 16, 1988, abandoned.

[30] Foreign Application Priority Data

Dec. 28, 1987 [CH] Switzerland .................. 5075/87

[51] Int. Cl.$^5$ ............................................. C07D 249/20
[52] U.S. Cl. ..................................... 548/261; 106/218; 548/113; 536/17.3
[58] Field of Search .................. 548/260, 259, 261

[56] References Cited

U.S. PATENT DOCUMENTS

| | | | |
|---|---|---|---|
| 3,218,332 | 11/1965 | Heller | 548/261 |
| 3,399,173 | 8/1968 | Heller et al. | 548/260 |
| 4,528,311 | 7/1985 | Beard et al. | 548/261 |
| 4,587,346 | 5/1986 | Winter et al. | 548/260 |
| 4,785,063 | 11/1988 | Slongo et al. | 548/260 |
| 4,853,471 | 8/1989 | Rody | 548/261 |
| 4,904,815 | 2/1990 | Howell | 560/75 |

FOREIGN PATENT DOCUMENTS

| | | |
|---|---|---|
| 0057160 | 8/1982 | European Pat. Off. . |
| 0131468 | 1/1985 | European Pat. Off. . |
| 0180548 | 5/1986 | European Pat. Off. ............ 548/260 |
| 0191582 | 8/1986 | European Pat. Off. . |
| 0323408 | 7/1989 | European Pat. Off. ............ 548/260 |
| 3624811 | 2/1988 | Fed. Rep. of Germany . |
| 1169859 | 11/1969 | United Kingdom . |

OTHER PUBLICATIONS

Chem Abst. 84, 155517g (1976).
Chem. Abst. 107, 31129f (1987).

Primary Examiner—Donald G. Daus
Attorney, Agent, or Firm—Luther A. R. Hall

[57] ABSTRACT

Benzotriazoles of the formula I

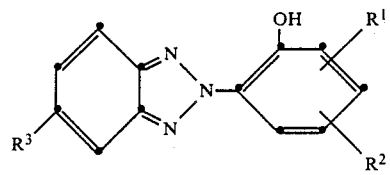

in which $R^1$ and $R^2$ are located in the ortho-position or para-position relative to the OH group and at least one of these substituents in an α-branched alkyl group containing a polar group M in the ω-position are liquid or low-melting compounds which absorb UV light and can be used as stabilizers for organic materials. M can be, for example, an ester or amide group. $R^3$ can be H, Cl, alkyl, alkoxy or a carboxyl group.

4 Claims, No Drawings

2-(2-HYDROXYPHENYL)-BENZOTRIAZOLE DERIVATIVES, SUBSTITUTED BY BRANCHED LONG CHAIN ALKYL GROUPS CONTAINING ESTER MOIETIES

This is a continuation-in-part application of application Ser. No. 285,680 filed Dec. 16, 1988.

The invention relates to novel derivatives of 2-(2-hydroxyphenyl)-benzotriazole and to their use as stabilizers.

Various derivatives of 2-(2-hydroxyphenyl)-benzotriazole are known, which are UV absorbers and are used as light stabilizers for various substrates, in particular for organic polymers. Most of these derivatives are crystalline compounds of a relatively high melting point. For certain substrates, for example for paints or for photographic image-recording materials, it is desirable to have light stabilizers with UV absorbing properties which are low-melting or liquid compounds. They should, in addition, be sparingly volatile.

Derivatives of 3-(benzotriazol-2-yl)-4-hydroxy-5-tert-butylphenylpropionic acid which are low-melting and dissolve readily in high-boiling solvents are described in EP-A 57,160. Their viscosity is too high, however, for use in the absence of a solvent.

In EP-A No. 189,374 the problem is solved by using technical mixtures of isomeric alkylation products. This has the disadvantage that it is difficult to prepare technical products of constant composition in a reproducible manner. In addition, it is difficult to determine impurities analytically in such mixtures.

Novel benzotriazole derivatives which can be used as light stabilizers in an excellent manner have now been developed.

These are compounds of the formula I

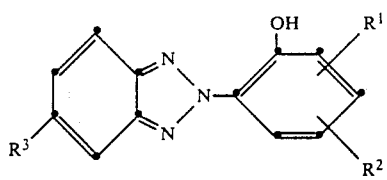

in which $R^1$ is located in the ortho-position or para-position relative to the OH group and is a group of the formula II

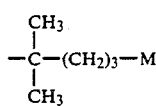

in which M is one of the following radicals:
(a) —COOR$^6$ or

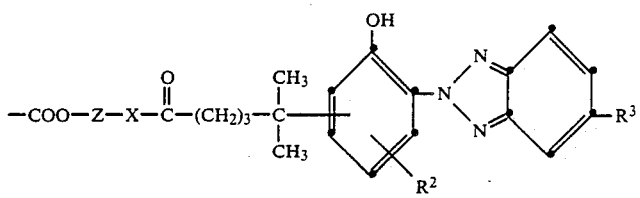

in which $R^6$ is hydrogen, $C_1$-$C_{18}$ alkyl which is unsubstituted or substituted by —OH, $C_3$-$C_{30}$alkyl or $C_3$-$C_{30}$hydroxyalkyl each of which is interrupted by one or more —O—, —S— or —N(R$^9$)— groups, $C_5$-$C_{12}$cycloalkyl, $C_2$-$C_{18}$alkenyl, $C_7$-$C_{15}$aralkyl, glycidyl or furfuryl each of which is unsubstituted or substituted by —OH, a group -CH$_2$-CH(OH)-R$^{10}$, a mono monosaccharide or disaccharide radical X is —O— or —N(R$^9$)—, Z is $C_2$-$C_8$alkylene, $C_4$-$C_8$alkynylene, $C_4$-$C_8$alkynylene, cyclohexylene, $C_4$-$C_{40}$alkylene which is interrupted by one or more —O— groups or is —CH$_2$CH(OH)CH$_2$—OR$^{11}$O—CH$_2$CH(OH)CH$_2$—, $R^9$ is hydrogen, $C_1$-$C_{18}$alkyl, $C_5$-$C_{12}$alkylene which is interrupted by one or more —O— groups or is —CH$_2$CH(OH)CH$_2$—OR$^{11}$O—CH$_2$CH(OH)CH$_2$—, $R^9$ is hydrogen, $C_1$-$C_{18}$alkyl, $C_5$-$C_{12}$cycloalkyl, $C_3$-$C_8$alkenyl, $C_6$-$C_{10}$aryl, $C_7$-$C_{18}$alkylaryl or $C_7$-$C_{15}$aralkyl, $R^{10}$ is phenyl, hydroxyphenyl, $C_7$-$C_{15}$aralkyl or —CH$_2$OR$^7$ where $R_7$ is $C_1$-$C_{18}$alkyl, $C_5$-$C_{12}$cycloalkyl, $C_2$-$C_5$alkenyl, $C_6$-$C_{10}$aryl, $C_7$-$C_{18}$alkylaryl pr $C_7$-$C_{15}$aralkyl and $R^{11}$ is $C_2$-$C_8$alkylene,
(b) —CO—N(R$^{12}$)(R$^{13}$) or

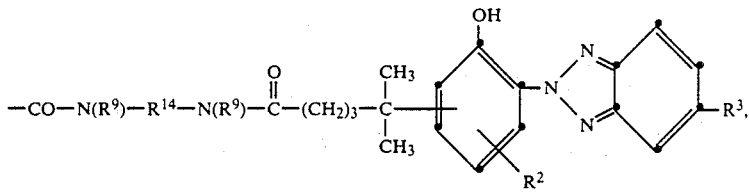

in which $R^{12}$ and $R^{13}$ independently of one another are H, $C_1$-$C_{18}$alkyl, $C_3$-$C_{30}$alkyl which is interrupted by one or more —O—, —S— or —N(R$^9$)— groups, $C_5$-$C_{12}$cycloalkyl, phenyl or phenyl which is substituted by $C_1$-$C_{12}$alkyl, $C_1$-$C_4$alkoxy or halogen, $C_3$-$C_8$alkenyl, $C_7$-$C_{15}$aralkyl or $C_2$-$C_4$hydroxyalky or $R^{12}$ and $R^{13}$ together are $C_4$-$C_6$alkylene or $C_4$-$C_6$alkylene which is interrupted by —O—, —S— or —N(R$^9$)— and $R^{14}$ is $C_2$-$C_{12}$alkylene, $R^2$ is located in the ortho-position or para-position relative to the OH group and is hydrogen, halogen, $C_1$-$C_{18}$alkyl, $C_7$-$C_9$phenylalkyl, $C_5$-$C_8$cycloalkyl, phenyl, a group of the formula II or a group of the formula IV $-C_pH_{2p}-COOR^6$      IV which p is 0, 1 or 2, and $R^3$ is hydrogen, chlorine, $C_1$-$C_4$alkyl, $C_1$-$C_4$alkoxy or $-COOR^6$.

If any substituents herein are alkyl, they can be linear or branched alkyl. The same applies to alkyl groups which are substituted or interrupted by heteroatoms. If any substituents are alkylene or alkylene interrupted by heteroatoms, unbranched or branched chains can be involved.

As hydroxyalkyl interrupted by O, $R^6$ is preferably a group $-CH_2CH_2$ in which x is 1-12.

As alkylaryl, $R^7$ and $R^9$ are preferably alkylphenyl.

If $R^{12}$ and $R^{13}$ or $R^{16}$ and $R^{17}$ are alkylene or alkylene which is interrupted by O, S or $N(R^9)$, they form, together with the N atom to which they are attached, a saturated heterocyclic ring, for example a pyrrolidine, piperidine, morpholine, thiomorpholine, piperazine or 4-methylpiperazine ring.

The substituent M is preferably
(a) a group $-COOR^6$ or

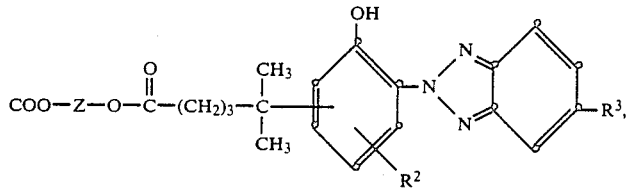

in which $R^6$ is hydrogen, $C_1$-$C_{18}$alkyl which is unsubstituted or substituted by $-OH$, $C_3$-$C_{20}$alkyl or $C_3$-$C_{20}$hydroxyalkyl each of which interrupted by one or more $-O-$ groups, $C_5$-$C_{12}$cycloalkyl, $C_2$-$C_{18}$alkenyl, $C_7$-$C_{15}$aralkyl, glycidyl or furfuryl each of which is unsubstituted or substituted by $-OH$, or is a group $-CH_2-CH(OH)-R^{10}$ and $R^{10}$ is phenyl, hydroxyphenyl, $C_7$-$C_{12}$aralkyl or $-CH_2OR^7$ and $R^7$ is $C_1$-$C_{18}$alkyl, cyclohexyl, phenyl, tolyl or benzyl, $R^{11}$ is $C_2$-$C_8$alkylene and $R^2$ and $R^3$, have the meanings given previously;

(b) a group $-CO-N(R^{12})(R^{13})$ or

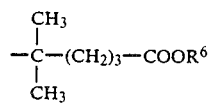

in which $R^{12}$ and $R^{13}$ independently of one another are H, $C_1$-$C_{12}$alkyl, $C_3$-$C_{20}$alkyl which is interrupted by $-O-$, $C_5$-$C_{12}$cycloalkyl, phenyl or phenyl which is substituted by $C_1$-$C_{12}$alkyl, $C_1$-$C_4$alkoxy or halogen, $C_3$-$C_8$alkenyl, $C_7$-$C_{11}$phenylalkyl or $C_2$-$C_4$hydroxyalkyl or $R^{12}$ and $R^{13}$ together are $C_4$-$C_5$alkylene or $C_4$-$C_6$alkylene which is interrupted by $-O-$ or $-N(R^9)-$, $R^{14}$ is $C_2$-$C_8$alkylene and $R^2$ and $R^3$ have the meanings given previously.

M is particularly preferably a group $-COOR^6$.

Compounds of the formula I which are preferred are those in which $R^1$ is a group of the formula II in which M has one of the meanings indicated previously, $R^2$ is $C_1$-$C_{12}$alkyl or a group of the formula II or a group of the formula IV in which p is 1 or 2, and $R^3$ is hydrogen, chlorine, $C_1$-$C_4$alkyl, $C_1$-$C_4$alkoxy or $-COOR^6$ in which $R^6$ has one of the meanings indicated previously, in particular compounds of the formula I in which $R^1$ is a group of the formula II in which M is a group $-COOR^6$ in which $R^6$ is hydrogen, $C_1$-$C_{18}$alkyl which is unsubstituted or substituted by $-OH$, $C_3$-$C_{30}$alkyl or $C_3$-$C_{30}$hydroxyalkyl each of which is interrupted by one or more, $-O-$ group, or $C_5$-$C_{12}$cycloalkyl, $C_2$-$C_{18}$alkenyl, $C_7$-$C_{15}$aralkyl, glycidyl or furfuryl each of which is unsubstituted or substituted by $-OH$, $R^2$ is $C_1$-$C_{12}$alkyl, $C_7$-$C_9$phenylalkyl, $C_5$-$C_8$cycloal the formula II or of the formula IV in which p is 1 or 2 and $R^3$ is hydrogen, chlorine, $C_1$-$C_4$alkyl, $C_1$-$C_4$alkoxy or $-COOR^6$.

Compounds of the formula I which are particularly preferred are those in which $R^1$ is a group of the formula IIa $$-\underset{\underset{CH_3}{|}}{\overset{\overset{CH_3}{|}}{C}}-(CH_2)_3-COOR^6 \qquad \text{IIa}$$

in which $R^6$ is $C_5$-$C_{18}$alkyl which is unsubstituted or substituted by $-OH$, $C_3$-$C_{30}$alkyl or $C_3$-$C_{30}$hydroxyalkyl each of which is interrupted by one or more $-O-$ groups, $C_5$-$C_{12}$cycloalkyl, $C_2$-$C_{18}$alkenyl, $C_7$-$C_{15}$aralkyl, glycidyl or furfuryl, $R^2$ is $C_1$-$C_{12}$alkyl, cyclohexyl or a group of the formula IIa or IV in which p is 1 or 2, and $R^3$ is hydrogen or chlorine.

Examples of compounds of the formula I are afforded by the following compounds of the formula

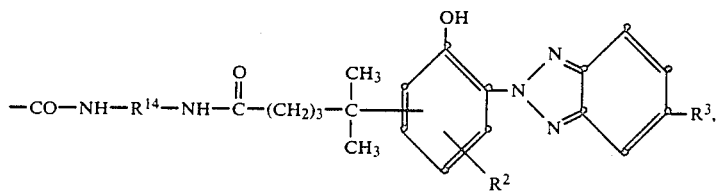

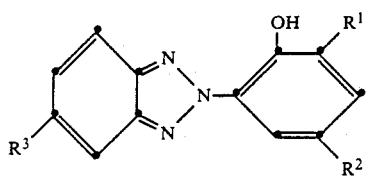

| R¹ | R² | R³ |
|---|---|---|
| —C(CH$_3$)$_2$CH$_2$CH$_2$CH$_2$COOCH$_3$ | —CH$_3$ | H |
| —C(CH$_3$)$_2$CH$_2$CH$_2$CH$_2$COOC$_8$H$_{17}$ | —C$_2$H$_5$ | H |
| —C(CH$_3$)$_2$CH$_2$CH$_2$CH$_2$COOC$_8$H$_{17}$ | —C(CH$_3$)$_2$CH$_2$CH$_2$CH$_2$COOC$_8$H$_{17}$ | H |
| —C(CH$_3$)$_2$CH$_2$CH$_2$CH$_2$COOC$_6$H$_{13}$ | —CH(CH$_3$)$_2$ | H |
| —C(CH$_3$)$_2$CH$_2$CH$_2$CH$_2$COOC$_{12}$H$_{25}$ | —C(CH$_3$)$_3$ | H |
| —C(CH$_3$)$_2$CH$_2$CH$_2$CH$_2$COOC$_4$H$_9$ | —C(CH$_3$)$_2$CH$_2$C(CH$_3$)$_3$ | H |
| —C(CH$_3$)$_2$CH$_2$CH$_2$CH$_2$COO(CH$_2$CH$_2$O)$_3$H | —C(CH$_3$)$_2$C$_2$H$_5$ | H |
| —C(CH$_3$)$_2$CH$_2$CH$_2$P(O)(OCH$_3$)(OH) | —CH$_3$ | H |
| —C(CH$_3$)$_2$CH$_2$CH$_2$CH$_2$CN | —CH$_2$Phenyl | H |
| —C(CH$_3$)$_2$CH$_2$CH$_2$CH$_2$CH(CH$_3$)NHCOCH$_3$ | —CH(CH$_3$)C$_2$H$_5$ | H |
| —C(CH$_3$)$_2$CH$_2$CH$_2$CH$_2$COOCH$_2$CH(C$_2$H$_5$)C$_4$H$_9$ | —CH$_3$ | —COOCH$_2$CH(C$_2$H$_5$)C$_4$H$_9$ |
| —C(CH$_3$)$_2$—(CH$_2$)$_3$—CH(CH$_3$)—CH$_2$CH$_2$OH | —C$_2$H$_5$ | H |
| —C(CH$_3$)$_2$CH$_2$CH$_2$CH$_2$COOC$_8$H$_{17}$ | —CH$_3$ | Cl |
| —C(CH$_3$)$_2$CH$_2$CH$_2$CH$_2$COOC$_8$H$_{17}$ | —CH(CH$_3$)$_2$ | —C$_2$H$_5$ |
| —C(CH$_3$)$_2$CH$_2$CH$_2$CH$_2$COOC$_8$H$_{17}$ | —CH$_2$COOC$_8$H$_{17}$ | H |
| —C(CH$_3$)$_2$CH$_2$CH$_2$CH$_2$COOC$_2$H$_5$ | —CH$_2$CH$_2$COOC$_2$H$_5$ | H |
| —C(CH$_3$)$_2$CH$_2$CH$_2$CH$_2$COOC$_8$H$_{17}$ | —CH$_2$CH$_2$COOC$_8$H$_{17}$ | H |
| —C(CH$_3$)$_2$CH$_2$CH$_2$CH(COOC$_4$H$_9$)$_2$ | —C(CH$_3$)$_2$-Phenyl | H |
| —C(CH$_3$)$_2$—(CH$_2$)$_3$—CH(CH$_3$)—CH$_2$CH$_2$OCOCH$_3$ | —CH$_3$ | H |
| —C(CH$_3$)$_2$CH$_2$CH$_2$CH$_2$COCH$_3$ | —C(CH$_3$)$_3$ | H |
| —C(CH$_3$)$_2$CH$_2$CH$_2$CH$_2$NHC$_8$H$_{17}$ | -Phenyl | H |
| —C(CH$_3$)$_2$CH$_2$CH$_2$CH$_2$COOC$_8$H$_{17}$ | —C(CH$_3$)$_2$CH$_2$CH$_2$CH$_2$NHC$_8$H$_{17}$ | H |
| —C(CH$_3$)$_2$CH$_2$CH$_2$CH$_2$COOC$_8$H$_{17}$ | —Cl | H |
| —C(CH$_3$)$_2$CH$_2$CH$_2$CH$_2$COOC$_8$H$_{17}$ | -Cyclohexyl | H |
| —C(CH$_3$)$_2$CH$_2$CH$_2$CH$_2$CH(CH$_3$)CH$_2$CH$_2$Br | —CH(CH$_3$)C$_2$H$_5$ | H |
| H$_3$C—⟨cyclohexyl⟩—COOCH$_2$CH(CH$_3$)C$_2$H$_5$ | —CH$_3$ | H |
| H$_3$C—⟨cyclohexyl⟩—CONHCH$_2$CH(C$_2$H$_5$)C$_4$H$_9$ | —CH$_3$ | H |
| —C$_2$H$_5$ | —C(CH$_3$)$_2$CH$_2$CH$_2$CH$_2$COOC$_5$H$_{11}$ | H |
| —CH(CH$_3$)$_2$ | —C(CH$_3$)$_2$CH$_2$CH$_2$CH$_2$COOCyclohexyl | H |
| —CH$_3$ | —C(CH$_3$)$_2$CH$_2$CH$_2$CH$_2$COCH$_3$ | H |
| —CH(CH$_3$)C$_2$H$_5$ | —C(CH$_3$)$_2$CH$_2$CH$_2$CH$_2$CN | H |
| —CH(CH$_3$)$_2$ | —C(CH$_3$)$_2$CH$_2$CH$_2$CH$_2$COOCH$_2$CH(CH$_3$)C$_2$H$_5$ | Cl |
| —H | —C(CH$_3$)$_2$CH$_2$CH$_2$CH$_2$CH(CH$_3$)NHCOCH$_3$ | H |
| —CH$_3$ | —C(CH$_3$)$_2$CH$_2$CH$_2$CH$_2$CH(CH$_3$)CH$_2$CH$_2$NO$_2$ | H |
| -Phenyl | —C(CH$_3$)$_2$CH$_2$CH$_2$CH$_2$COOCH$_2$CH(CH$_3$)C$_2$H$_5$ | H |
| —C$_2$H$_5$ | —C(CH$_3$)$_2$CH$_2$CH$_2$CH$_2$CONHCH$_2$CH(C$_2$H$_5$)C$_4$H$_9$ | H |
| —H | —C(CH$_3$)$_2$CH$_2$CH$_2$CH$_2$COOCH$_2$CH(CH$_3$)C$_2$H$_5$ | H |
| —CH(CH$_3$)$_2$ | —C(CH$_3$)$_2$CH$_2$CH$_2$CH$_2$COOCH$_2$CH(C$_2$H$_5$)C$_4$H$_9$ | H |
| —CH(CH$_3$)C$_2$H$_5$ | —C(CH$_3$)$_2$CH$_2$CH$_2$CH$_2$COO(CH$_2$CH$_2$O)$_3$H | H |
| —CH(CH$_3$)$_2$ | —C(CH$_3$)$_2$CH$_2$CH$_2$CH$_2$COO(CH$_2$CH$_2$O)$_3$CH$_3$ | H |
| —CH(CH$_3$)$_2$ | —C(CH$_3$)$_2$CH$_2$CH$_2$CH$_2$CON(C$_8$H$_{17}$)$_2$ | H |
| —C$_2$H$_5$ | —C(CH$_3$)$_2$CH$_2$CH$_2$CH$_2$COOCH$_2$P(O)(OC$_4$H$_9$)$_2$ | H |
| —C$_2$H$_5$ | —C(CH$_3$)$_2$CH$_2$CH$_2$CH$_2$COOCH$_2$P(O)(OCH$_3$)$_2$ | H |
| —C$_2$H$_5$ | —C(CH$_3$)$_2$CH$_2$CH$_2$CH$_2$COOCH$_2$CH(OH)CH$_2$P(O)(OC$_2$H$_5$)$_2$ | H |
| —CH(CH$_3$)$_2$ | —C(CH$_3$)$_2$CH$_2$CH$_2$CH$_2$COOCH$_2$CH(OH)C$_6$H$_{13}$ | H |
| —CH(CH$_3$)$_2$ | —C(CH$_3$)$_2$CH$_2$CH$_2$CH$_2$COOCH$_2$CH(OH)CH$_2$OC$_8$H$_{17}$ | H |

Further examples of compounds of the formula I are afforded by the following compounds of the formula

| | | | |
|---|---|---|---|
| ![structure] HO—C(CH₃)₂—(CH₂)₃—CO—R—CO—(CH₂)₃—(CH₃)₂C—OH (bis-benzotriazole with R³, R²) | | | |
| R | R² | R³ | |
| —OCH₂CH₂O— | —CH(CH₃)₂ | H | |
| —O(CH₂)₄O— | —CH₃ | Cl | |
| —OCH₂CH₂NH— | —CH₃ | H | |
| —O(CH₂CH₂O)₃— | —C₂H₅ | H | |
| —O(CH₂CH₂O)₈— | —CH(CH₃)C₂H₅ | H | |
| —O—⟨cyclohexylene⟩—O— | —CH₃ | H | |
| | —CH₃ | | |
| —NH—(CH₂)₆—NH— | —CH(CH₃)C₂H₅ | H | |
| —N(C₄H₉)—(CH₂)₆—N(C₄H₉)— | —C₂H₅ | H | |

Further examples of compounds of the formula I are afforded by the following compounds of the formula

| R | R¹ | R³ |
|---|---|---|
| —OCH₂CH₂O— | —C₂H₅ | H |
| —O(CH₂CH₂O)₃— | —CH(CH₃)₂ | H |
| —O(CH₂CH₂O)₈— | —CH₃ | Cl |
| —OCH₂CH₂NH— | —CH(CH₃)C₂H₅ | H |
| —O—(CH₂)₆—O— | —CH(CH₃)₂ | H |

The compounds of the formula I are novel compounds.

They can be prepared analogously to other 2.(2.hydroxyphenyl)-benzotriazoles. The most important process for their preparation is a multi-stage synthesis starting from an o-nitroaniline, which is diazotized to give the corresponding diazonium salt VII. The diazonium salt VII is coupled with a substituted phenol VIII with the formation of the azo dye IX. The benzotriazole I is formed by reduction of IX:

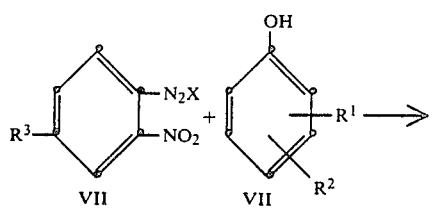

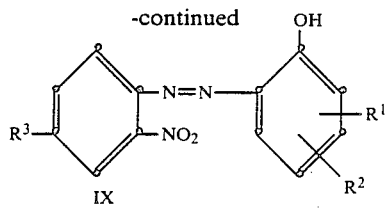

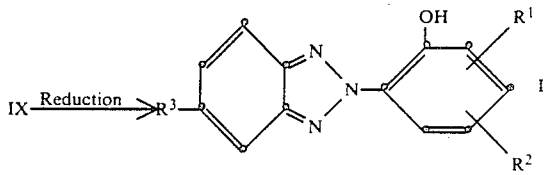

The reduction can be effected, for example, catalytically by means of H₂, Zn or various organic reducing agents. The corresponding processes for reducing are known from the literature.

Substituted phenols of the formula VIII are described, for example, in EP-A No. 106,799. A group M is already present in the group R¹ of the phenol VIII. It can be converted into other groups M by known methods after the formation of the benzotriazole I. In this case, compounds of the formula I are used as intermediates for the preparation of other compounds of the formula I.

For example, M can initially be a carboxyl group, which, after the formation of the benzotriazole, is halogenated, esterified or amidated. If M is initially a hydroxyl group, it can be halogenated or esterified after the formation of the benzotriazole. If M is initially a halogen, this can subsequently be converted, for example, into an alkoxy group, amino group, phosphonate group or cyano group.

If M is a group —COOR$^6$ in which R$^6$ is a lower alkyl group, the compound can be transesterified with a higher alcohol to give the corresponding ester in which R$^6$ is a higher alkyl radical or an aralkyl or cycloalkyl radical. The lower alkyl ester is thus an intermediate for the higher ester in this case.

The compounds of the formula I can be used as stabilizers for organic materials, in particular to stabilize them against damage caused by light, oxygen and heat.

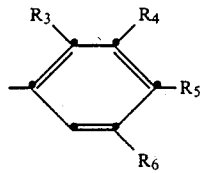

in which R$_3$ is hydrogen, halogen, alkyl or alkoxy and R$_4$, R$_5$ and R$_6$ are hydrogen, halogen, alkyl, alkenyl, alkoxy, aryl, carboxyl, alkoxycarbonyl, a carbamoyl group, a sulfone or sulfamoyl group, an alkylsulfonamido group, an acylamino group, a ureido group or an amino group. Preferably, R$_3$ is chlorine, R$_4$ and R$_5$ are hydrogen and R$_6$ is an acylamino group. The compound of the formula

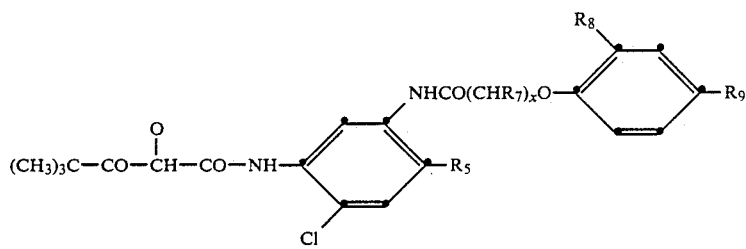

in which x is 0–4, R$_7$ is hydrogen or alkyl and R$_8$ and R$_9$ are alkyl are also included amongst these.

Another group of yellow couplers corresponds to the formula B

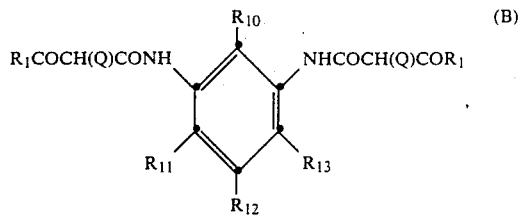

in which R$_{10}$ is hydrogen, halogen or alkoxy, R$_{11}$, R$_{12}$ and R$_{13}$ are hydrogen, halogen, alkyl, alkenyl, alkoxy, aryl, carboxyl, alkoxycarbonyl, a carbamoyl group, a sulfamoyl group, a sulfonamido group, an acylamino group, ureido group or an amino group and R$_1$ and Q are as defined above.

Compounds of the formula B in which R$_1$ is t-butyl, R$_{10}$ is chlorine, R$_{11}$ and R$_{13}$ are hydrogen and R$_{12}$ is alkoxycarbonyl are included amongst these.

In the compounds of the formula A and B the detachable group Q can be hydrogen or is a heterocyclic group They are particularly effective as light stabilizers. The materials to be stabilized can be, for example, oils, fats, waxes, cosmetics, photographic materials or organic polymers.

Photographic materials which can be stabilized are photographic dyes and emulsions containing such dyes or precursors thereof, for example photographic papers and films.

It is known that light stabilizers often tend to crystallize out in layers of photographic materials and thus impair the photographic quality of the materials. The inventive compounds, however, when incorporated in such layers do not show this tendency which renders them particularly useful as light stabilizers in photographic materials. The stabilizers according to the invention can be added to one or two or all three colour-sensitive layers. Their addition to the yellow layer is particularly important. The sensitized silver halide and the particular dye coupler are present in the layers.

In addition, the layers can contain further stabilizers and/or other additives.

The yellow couplers are preferably compounds of the formula A

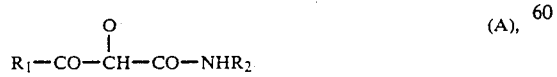
(A), in which R$_1$ is alkyl or aryl, R$_2$ is aryl and Q is hydrogen or a group which can be removed by reaction with the oxidized developer. One group of yellow couplers is formed by compounds of the formula A in which R$_1$ is t-butyl and R$_2$ is a group of the formula

in which R$_{14}$ is an organic divalent group which completes the ring to form a 4-membered to 7-membered ring, or Q is a group —OR$_{15}$ in which R$_{15}$ is alkyl, aryl, acyl or a heterocyclic radical.

The compounds of the following formulae are typical examples of customary yellow couplers:

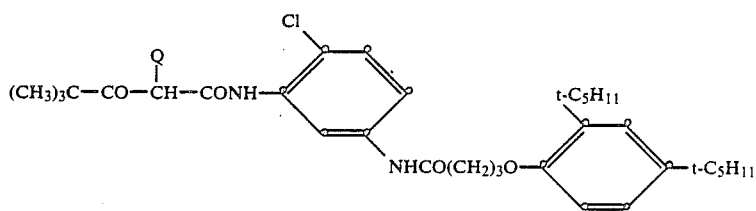
(a) Q = 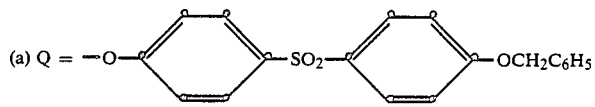
(b) Q = 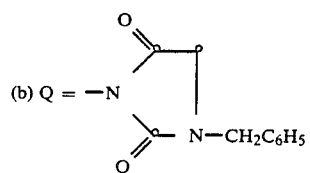
(c) Q = 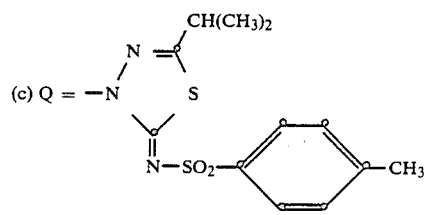
(d) Q = 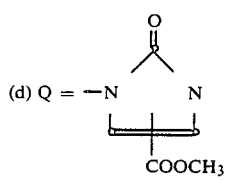
(e) Q = 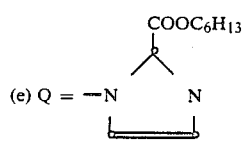
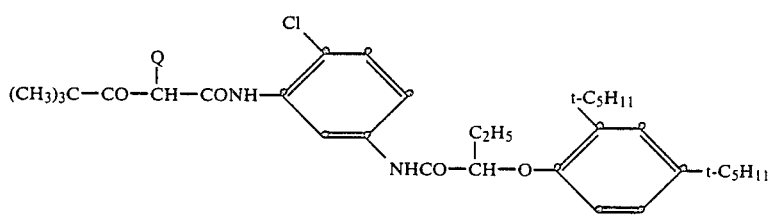
(f) Q = 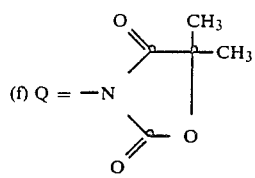   (g) Q = 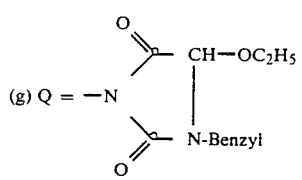

-continued

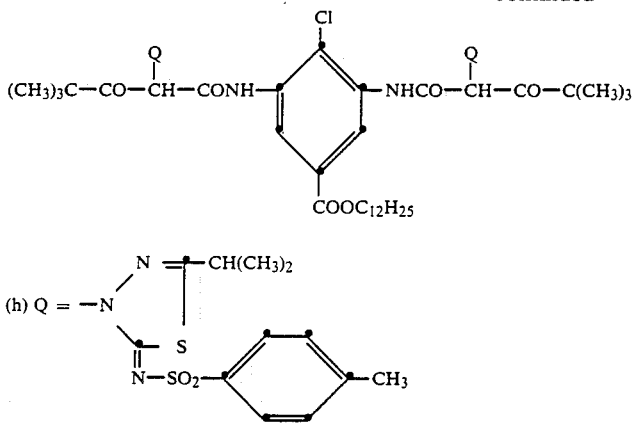

Further examples of yellow couplers are to be found in US-A No. 2,407,210, 2,778,658, 2,875,057, 2,908,513, 2,908,573, 3,227,155, 3,227,550, 2,253,924, 3,265,506, 3,277,155, 3,408,194, 3,341,331, 3,369,895, 3,384,657, 3,415,652, 3,447,928, 3,551,155, 3,582,322, 3,725,072, 3,891,445, 3,933,501, 4,115,121, 4,401,752, and 4,022,620, in DE-A No. 1,547,868, 2,057,941, 2,162,899, 2,163,813, 2,213,461, 2,219,917, 2,261,361, 2,261,362. 2,263,875, 2,329,587, 2,414,006, and 2,422,812 and in GB-A No. 1,425,020 and 1,077,874.

The yellow couplers are generally used in an amount of 0.05-2 mole, preferably 0.1-1 mole, per mole of silver halide.

Magenta couplers can be, for example, simple 1-aryl-5-pyrazolones or pyrazole derivatives which are condensed with 5-membered heterocyclic rings, for example imidazopyrazoles, pyrazolopyrazoles, pyrazolotriazoles or pyrazolttetrazoles.

One group of magenta couplers is formed by 5-pyrazolones of the formula C

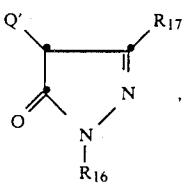   (C)

such as are described in British Patent Specification No. 2,003,473. In this formula $R_{16}$ is hydrogen, alkyl, aryl, alkenyl or a heterocyclic group. $R_{17}$ is hydrogen, alkyl, aryl, a heterocyclic group an ester group, an alkoxy group, an alkylthio group, a carboxyl group, an arylamino group, an acylamino group, a (thio)urea group, a (thio)carbamoyl group, a guanidino group or a sulfonamide group.

$R_{17}$ is preferably a group 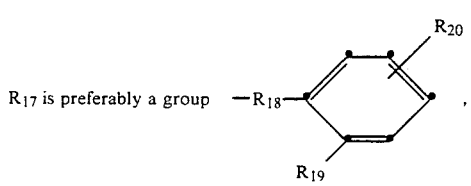

in which $R_{18}$ is imino, acylamino or ureido, $R_{19}$ is hydrogen, halogen, alkyl or alkoxy and $R_{20}$ is hydrogen alkyl, acylamino, carbamoyl, sulfamoyl, sulfonamido, alkoxycarbonyl, acyloxy or a urethane group.

If Q' is hydrogen, the magenta coupler is tetra-equivalent relative to the silver halide.

Typical examples of this type of magenta couplers are compounds of the formula

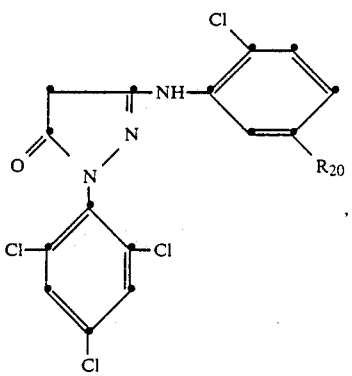

in which $R_{20}$ is as defined above.

Further examples of such tetra-equivalent magenta couplers are to be found in US-A No. 2,983,608, 3,061,432, 3,062,653, 3,127,269, 3,152,896, 3,311,476, 3,419,391, 3,519,429, 3,558,319, 3,582,322, 3,615,506, 3,684,514, 3,834,908, 3,888,680, 3,891,445, 3,907,571, 3,928,044, 3,930,861, 3,930,866 and 3,933,500.

If Q' in formula C is not hydrogen but a group which is eliminated in the course of the reaction with the oxidized developer, the magenta coupler is di-equivalent. In this case Q can be, for example, halogen or a group attached to the pyrazole ring via O, S or N. Di-equivalent couplers of this type give a higher colour density and are more reactive towards the oxidized developer than the corresponding tetra-equivalent magenta couplers.

Examples of di-equivalent magenta couplers are described in US-A No. 3,006,579, 3,419,391, 3,311,476, 3,432,521, 3,214,437, 4,032,346, 3,701,783, 4,351,897, and 3,227,554, in EP-A No. 133,503, DE-A No. 2,944,601 and JP-A No. 78/34,044, 74/53,435, 74/53,436, 75/53,372 and 75/122,935.

2 Pyrazolone rings can be attached via a divalent Q' and so-called biscouplers are then obtained Couplers of this type are described, for example, in US-A No. 2,632,702 and 2,618,864. GB-A No. 968,461 and 786,859 and JP-A No. 76/37,646, 59/4,086, 69/16,110, 69/26,589, 74/37,854 and 74/29,638. Y is preferably an O-alkoxyarylthio group. As mentioned above, pyrazoles condensed with 5-membered heterocyclic structures—so-called pyrazoloazoles —can also be used as magenta couplers. The advantages of these over simple Pyrazoles are that they display colours of greater resistance to formaldehyde solution and purer absorption spectra.

They can be represented by the general formulae $D_1$ and $D_2$

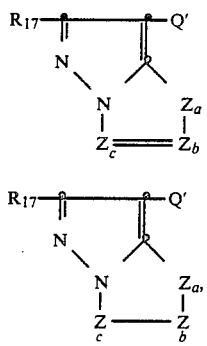

in which $Z_a$, $Z_b$ and $Z_c$ are the remaining members of a 5-membered ring which can contain up to 4 nitrogen atoms. Accordingly, the compounds can be pyrazolo-imidazoles, pyrazolo-pyrazoles, pyrazolo-triazoles or pyrazolo-tetrazoles. $R_{17}$ and $Q'$ are as defined in formula C.

Pyrazolo-tetrazoles are described in JP-A No. 85/33,552; pyrazolo-pyrazoles in JP-A No. 85/43,695; pyrazolo-imidazoles in JP-A No. 85/35,732, JP-A No. 86/18,949 and US-A No. 4,500,630; and pyrazolo-triazoles in JP-A No. 85/186,567, JP-A No. 86/47,957, JP-A No. 85/215,687, JP-A No. 85/197,688. and JP-A 85/172,982, EP-A No. 119,860, EP-A No. 173,256, EP-A No. 178,789, and EP-A No. 178,788 and in Research Disclosure 84/24,624.

Further pyrazoloazole magenta couplers are described in JP-A No. 86/28,947, JP-A No. 85/140,241, JP-A No. 85/262,160 and JP-A No. 85/213,937, EP-A No. 177,765, EP-A No. 176,804, EP-A No. 170,164 EP-A No. 164,130, and EP-A No. 178,794, DE-A No. 3.516.996 and DE-A No. 3.508.766 and Research Disclosure 81/20,919, 84/24,531 and 85/25,758.

Cyan couplers can be, for example, derivatives of phenol, 1-naphthol or pyrazoloquinazolone. Structures of the formula E

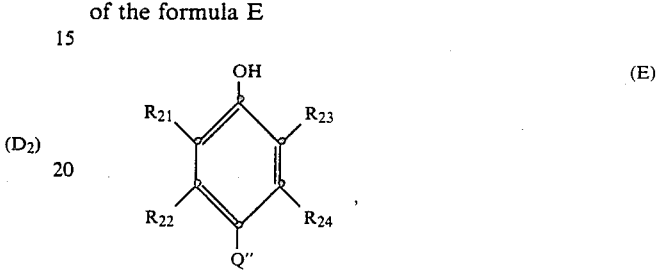

in which $R_{21}$, $R_{22}$, $R_{23}$ and $R_{24}$ are hydrogen, halogen. alkyl, carbamoyl, amido, sulfonamido, phosphoramido or ureido are preferred. $R^{21}$ is preferably H or Cl and $R_{22}$ is preferably an alkyl or amido group. $R_{23}$ is preferably an amido group and $R_{24}$ is preferably hydrogen. $Q''$ is hydrogen or a detachable group which is split off in the reaction with the oxidized developer. A detailed enumeration of cyan couplers is to be found in US-A No. 4,456,681.

The following are examples of customary cyan couplers:

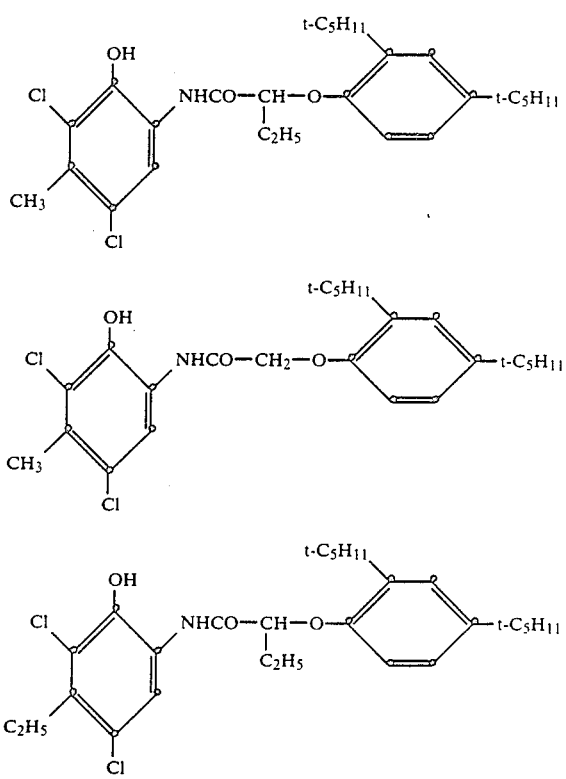

-continued

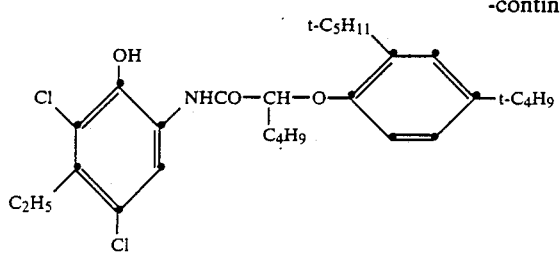

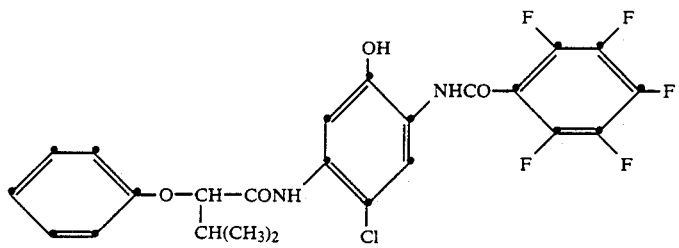

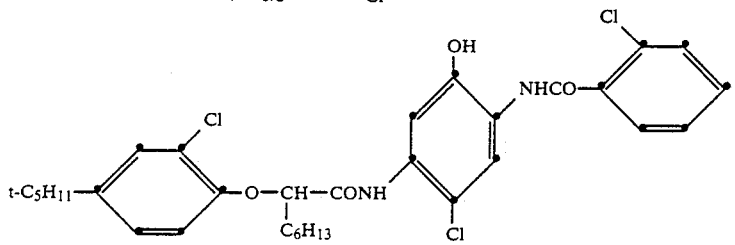

Further examples of cyan couplers are to be found in the following US-A texts: 2,369,929, 2,423,730, 2,434,272, 2,474,293, 2,521,908, 2,698,794, 2,706,684, 2,772,162, 2,801,171, 2,895,826, 2,908,573, 3,034,892, 3,046,129, 3,227,550 3,253,294, 3,311,476, 3,386,301, 3,419,390, 3,458,315, 3,476,560, 3,476,563, 3,516,831, 3,560,212, 3,582,322, 3,583,971, 3,591,383, 3,619,196, 3,632,347, 3,652,286, 3,737,326, 3,758,308, 3,839,044, 3,880,661, 4,004,929, 4,124,396, 4,333,999, 4,463,086 and 4,456,681.

The colour developers customarily used for colour photographic materials are p-dialkylaminoanilines. Examples of these are 4-amino-N,N-diethylaniline-3-methyl-4-amino-N,N-diethylaniline, 4-amino-N-ethyl-N-α-hydroxyethylaniline, 3-methyl-4-amino-N-ethyl-N-α-hydroxyethylaniline, 3-methyl-4-amino-N-ethyl-N-α-methanesulfonamidoethylaniline, 3-methyl-4-amino-N-ethyl-N-α-methoxy-ethyl-aniline, 3-α-methanesulfonamidoethyl-4-amino-N,N-diethylaniline, 3-methoxy-4-amino-N-ethyl-N-α-hydroxyethylaniline, 3-methoxy-4-amino-N-ethyl-N-α-methoxyethylaniline, 3-acetamido-4-amino-N,N-diethylaniline, 4-amino-N,N-dimethylaniline, N-ethyl-N-α-[α'-(α''-methoxyethoxy)ethoxy]ethyl-3-methyl-4-aminoaniline, N-ethyl-N-α-(α'-methoxyethoxy)ethyl-3-methyl-4-aminoaniline and the salts of such compounds, for example sulfates, hydrochlorides or toluenesulfonates.

The stabilizers according to the invention can be incorporated into the colour photographic material on their own or together with the colour coupler and, if appropriate, further additives, by dissolving them beforehand in high-boiling organic solvents It is preferable to use solvents boiling above 160° C. Typical examples of such solvents are the esters of phthalic acid, phosphoric acid, citric acid, benzoic acid or fatty acids, and also alkylamides and phenols.

In most cases a low-boiling solvent is also used additionally in order to facilitate the incorporation of the additives into the colour photographic material. Examples of such solvents are esters, for example ethyl acetate, alcohols, for example butanol, ketones, for example methyl isobutyl ketone, chlorinated hydrocarbons, for example methylene chloride, or amides, for example dimethylformamide. If the additives themselves are liquid, they can also be incorporated into the photographic material without the aid of solvents.

Further details concerning high-boiling solvents which can be used are to be found in the following publications. Phosphates: GB-A No. 791,219, BE-A No. 755,248 and JP-A No. 76/76,739, 78/27,449, 78/218,252, 78/97,573, 79/148,113, 82/216,177, 82/93,323 and 83/216,177. Phthalates: GB-A No. 791,219 and JP-A No. 77/98,050, 82/93,322, 82/216,176, 82/218,251, 83/24,321, 83/45,699 and 84/79,888. Amides: GB-A No. 791,219, JP-A No. 76/105,043, 77/13,600, 77/61,089, and 84/189,556 and US-A No. 928,741. Phenols: GB-A No. 820,329. FR-A No. 1,200,657 and JP-A No. 69/69,946, 70/3,818, 75/123,026, 75/82,078, 78/17,914, 78/21,166, 82/212,114 and 83/45.699.

Other oxygen-containing compounds US-A No. 3,748,141 and 3,779,765, JP-A No. 73/75,126, 74/101,114, 74/10,115, 75/101,625, 76/76,740. and 77/61,089 and BE-A No. 826,039.

Other compounds: JP-A No. 72/115,369, 72/130,258, 73/127,521, 73/76,592, 77/13,193, 77/36,294, and 79/95,233 and Research Disclosure 82/21,918.

The amount of high-boiling solvent is, for example, within the range from 0.1 to 300%, preferably 10 to 100%, relative to the colour coupler.

The photographic layers can also contain colour cast inhibitors. These prevent the formation of colour cast such as is formed, for example, by the coupler reacting with unintentionally oxidized developer or with by-products of the colour formation process. Colour cast inhibitors of this type are in most cases hydroquinone derivatives, but can also be derivatives of aminophenols, gallic acid or ascorbic acid. Typical examples of these are to be found in the following publications: US-A No. 2,360,290, 2,336,327, 2,403,721, 2,418,613, 2,675,314, 2,701,197, 2,704,713, 2,728,659, 2,732,300, and 2,735,365; EP-A No. 124,877; and JP-A No. 75/92,988, 75/92,989, 75/93,928, 75/110,337 and 77/146,235.

The photographic layers can also contain so-called DIR couplers (DIR means Development Inhibition Release) which, with the oxidized developer, produce colourless compounds. They are added to improve the sharpness and grain of the colour images.

The photographic layers can also contain UV absorbers. These filter out the UV light and thereby protect the dyes, the couplers or other components against degradation by light. Examples of UV absorbers of this type are 2-(2-hydroxyphenyl)-benzotriazoles, 2-hydroxybenzophenones, salicyclic acid esters, acrylonitrile derivatives or thiazolines UV absorbers of this type are illustrated in greater detail in, for example, the following publications: US-A No. 3,314,794, 3,352,681, 3,705,805, 3,707,375, 4,045,229, 3,700,455, 3,533,794, 3,698,907, 3,705,805, and 3,738,837 and JP-A No. 71/2,784. The preferred UV absorbers are the 2-(2-hydroxyphenyl)-benzotriazoles.

The photographic layers can also contain phenolic compounds which act as a light stabilizer for the colour image and as an agent against colour cast. They can be present, on their own or together with other additives, in a light-sensitive layer (dye layer) or in an intermediate layer. Compounds of this type are described in greater detail in, for example, the following publications: US-A No. 3,700,455, 3,591,381, 3,573,052, 4,030,931, 4,174,220, 4,178,184, 4,228,235, 4,279,990, 4,346,165, 4,366,226, 4,447,523, 4,528,264, 4,581,326, 4,562,146 and 4,559,297; GB-A No. 1,309,277, 1,547,302, 2,023,862, 2,135,788, 2,139,370 and 2,156,091; DE-A No. 2,301,060, 2,347,708, 2,526,468, 2,621,203, and 3,323,448, DD-A No. 200,691 and 214,468; EP-A No. 106,799, 113,124, 125,522, 159,912, 161,577, 164,030, 167,762 and 176,845; JP-A No. 74/134,326, 76/127,730, 76/30,462, 77/3,822, 77/154,632, 78/10,842, 79/48,535, 79/70,830, 79/73,032, 79/147,038, 79/154,325, 79/155,836, 82/142,638, 83/224,353, 84/5,246, 84/72,443, 84/87,456, 84/192,246, 84/192,247, 84/204,039, 84/204,040, 84/212,837, 84/220,733, 84/222,836, 84/228,249, 86/2,540, 86/8,843, 86/18,835, 86/18,836, 87/11,456, 87/42,245, 87/62,157 and 86/6,652 and in Research Disclosure 79/17,804.

The photographic layers can also contain certain phosphorus-III compounds, in particular phosphites and phosphonites. These act as a light stabilizer for the colour images and as a dark storage stabilizer for magenta couplers They are preferably added, together with the coupler, to the high-boiling solvents. Phosphorus-III compounds of this type are described in greater detail in, for example the following publications: US-A No. 4,407,935 and 4,436,811, EP-A No. 181,289 and JP-A No. 73/32,728, JP-A No. 76/1,420 and JP-A No. 5/67,741.

The photographic layers can also contain organometallic complexes which are light stabilizers for the colour images, in particular for the magenta dyes. Compounds of this type and their combination with other additives are described, in greater in, for example, the following publications: US-A No. 4,050,938, 4,239,843, 4,241,154, 4,242,429, 4,241,155, 4,242,430, 4,273,854, 4,246,329, 4,271,253, 4,242,431, 4,248,949, 4,245,195, 4,268,605, 4,246,330, 4,269,926, 4,245,018, 4,301,223, 4,343,886, 4,346,165, and 4,590,153; JP-A No. 81/167,138, 81/168,652, 82/30,834 and 82/161,744; EP-A No. 137,271, 161,577 and 185,506; and DE-A No. 2,853,865.

The photographic layers can also contain hydroquinone compounds. These act as a light stabilizer for the colour couplers and for the colour images and as an inceptor of oxidized developer in intermediate layers. They are used particularly in the magenta layer. Hydroquinone compounds of this type and their combinations with other additives are described in greater detail in, for example, the following publications US-A No. 2,360,290, 2,336,327, 2,403,721, 2,418,613, 2,675,314, 2,701,197, 2,710,801, 2,732,300, 2,728,659, 2,735,765, 2,704713, 2,937,086, 2,816,028, 3,582,333, 3,637,393, 3,700,453, 3,960,570, 3,935,016, 3,930,866, 4,065,435, 3,982,944, 4,232,114, 4,121,939, 4,175,968, 4,179,293, 3,591,381, 3,573,052, 4,279,990, 4,429,031, 4,346,165, 4,360,589, 4,346,167, 4,385,111, 4,416,978, 4,430,425, 4,277,558, 4,489,155, 4,504,572, and 4,559,297, FR-A No. 885,982; GB-A No. 891,158, 1,156,167, 1,363,921, 2,022,274, 2,066,975, 2,071,348, 2,081,463, 2,117,526 and 2,156,091; DE-A No. 2,408,168, 2,726,283, 2,639,930, 2,901,520, 3,308,766, 3,320,483, and 3,323,699; DD-A No. 216,476, 214,468 and 214,469. EP-A No. 84,290, 110,214, 115,305, 124,915, 124,877, 144,288, 147,747, 178,165, and 161,577; JP-A No. 75/33,733, 5/21,249, 77/128,130, 77/146,234, 79/70,036, 79/133,131, 81/83,742, 1/87,040, 81/109,345, 83/134,628, 82/22,237, 82/112,749, 83/17,431, 3/21,249, 84/75,249, 84/149,348, 84/182,785, 84/180,557, 84/189,342, 4/228,249, 84/101,650, 79/24,019, 79/25,823, 86/48 856, 86/48,857, 86/27,539, 86/6,652, 86/72,040, 87/11,455, and 87/62,157 and in Research Disclosure 79/17,901, 79/17,905, 79/18,813, 83/22,827 and 84/24,014.

The photographic layers can also contain derivatives of hydroquinone ethers. These compounds act as light stabilizers and are particularly suitable for stabilizing magenta dyes. Compounds of this type and their combination with other additives are described in greater detail in, for example, the following publications:

US-A No. 3,285,937, 3,432,300, 3,519,429, 3,476,772, 3,591,381, 3,573,052, 3,574,627, 3,573,050, 3,698,909, 3,764,337, 3,930,866, 4,113,488, 4,015,990, 4,113,495, 4,120,723, 4,155,765, 4,159,910, 4,178,184, 4,138,259, 4,174,220, 4,148,656, 4,207,111, 4,254,216, 4,314,011, 4,273,864, 4,264,720, 4,279,990, 4,332,886, 4,436,165, 4,360,589, 4,416,978, 4,385,111, 4,459,015 and 4,559,297; GB-A No. 1,347,556, 1,366,441, 1,547,392, 1,557,237 and 2,135,788, DE-A No. 3,214,567, DD No. 214,469; EP-A No. 161,577, 167,762, 164,130 and 176,845; JP-A No. 76/123,642, 77/35,633, 77/147,433, 78/126,78/10,430, 78/53,321, 79/24,019, 79/25,823. 79/48,537, 79/44,521, 79/56,833, 79/70,036, 79/70.830, 79/73,032, 79/95,233, 79/145,530, 80/21,004, 80/50,244, 80/52,057, 80/70,840, 80/139,383, 81/30,125, 81/151,936, 82/34,552, 82/68,833, 82/204,036, 82/204,037, 83/134,634, 83/207,039, 84/60,434, 84/101,650, 84/87,450, 84/149,348, 84/182,785, 86/72,040, 87/11,455, 87/62,157, 87/63,149, 86/2.151, 86/6,652 and 86/48,855 and in Research Disclosure 78/17,051.

The following classes of polymers are examples of organic polymers which can be stabilized by means of the benzotriazoles according to the invention.

1. Polymers of monoolefins and diolefins, for example polypropylene, polyisobutylene, polybut-1-ene, poly-methylpent-1-ene, polyisoprene or polybutadiene and polymers of cycloolefins, for example cyclopentene or norbornene; and also polyethylene (which can, if appropriate, be cross-linked), for example high-density polyethylene (HDPE), low-density polyethylene (LDPE) or linear, low-density polyethylene (LLDPE)

2. Mixtures of the polymers mentioned under (1), for example mixtures of polypropylene and polyisobutylene. polypropylene and polyethylene (for example PP/HDPE or PP/LDPE) and mixtures of different types of polyethylene (for example LDPE/HDPE).

3. Copolymers of monoolefins and diolefins with one another or with other vinyl monomers, for example ethylene/propylene copolymers, linear low-density polyethylene (LLDPE) and mixtures thereof with low-density polyethylene (LDPE), propylene/but-1-ene copolymers, propylene/isobutylene copolymers, ethylene/but-1-ene copolymers, ethylene/hexene copolymers, ethylene/methylpentenecopolymers-ethylene/heptenecopolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and salts thereof (ionomers), and also terpolymers of ethylene with propylene and a diene, such as hexadiene, dicyclopentadiene or ethylidenenorbornene; and also mixtures of such copolymers with one another and with polymers mentioned under (1), for example polypropylene-ethylene propylene copolymers, LDPE-ethylene/vinyl acetate copolymers, LDPE-ethylene/acrylic acid copolymers, LLDPE-ethylene/vinyl acetate copolymers and LLDPE-ethylene/acrylic acid copolymers.

3a. Hydrocarbon resins (for example $C_5$–$C_9$), including hydrogenated modifications thereof (for example tackifier resins).

4. Polystyrene, poly-(p-methylstyrene) and poly-(α-methylstyrene).

5. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/maleic anhydride or styrene/acrylonitrile/methyl acrylate, mixtures of high impact strength formed from styrene copolymers and another polymer, for example a polyacrylate, a diene polymer or an ethylene/propylene/diene terpolymer; and also block copolymers of styrene, for example styrene/butadiene/styrene, styrene/isoprene/styrene-styrene/ethylene-butylene/styreneorstyrene/ethylene-propylene/styrene.

6. Graft copolymers of styrene or α-methylstyrene, for example styrene on polybutadiene, styrene on polybutadiene-styrene or polybutadiene-acrylonitrile copolymers, or styrene and acrylonitrile (or methacrylonitrile) on polybutadiene, styrene, acrylonitrile and methyl methacrylate on polybutadiene; styrene and maleic anhydride on polybutadiene; styrene, acrylonitrile and maleic anhydride or maleiimide on polybutadiene; styrene and maleiimide on polybutadiene, styrene and alkyl acrylates or alkyl methacrylates on polybutadiene, styrene and acrylonitrile on ethylene/propylene/diene terpolymers, styrene and acrylonitrile on polyalkyl acrylates or polyalkyl methacrylates, styrene and acrylonitrile on acrylate/butadiene copolymers and mixtures thereof with the copolymers mentioned under (5), such as are known, for example, as so-called ABS, MBS, ASA or AES polymers.

7. Halogen-containing polymers, for example polychloroprene, chlorinated rubber, chlorinated or chlorosulfonated polyethylene, epichlorohydrin homopolymers and copolymers, in particular polymers formed from halogen-containing vinyl compounds, for example polyvinyl chloride, polyvinylidene chloride, polyvinyl fluoride or polyvinylidene fluoride; and copolymers thereof, such as vinyl chloride/vinylidene chloride, vinyl chloride/vinyl acetate or vinylidene chloride/vinyl acetate.

8. Polymers derived from α-β-unsaturated acids and derivatives thereof, such as polyacrylates and polymethacrylates, polyacrylamides and polyacrylonitriles.

9. Copolymers of the monomers mentioned under (8) with one another or with other unsaturated monomers, for example acrylonitrile/butadiene copolymers, acrylonitrile/alkyl acrylate copolymers, acrylonitrile/alkoxy),alkyl acrylate copolymers, acrylonitrile/vinyl halide copolymers or acrylonitrile/alkyl methacrylate/butadiene terpolymers.

10. Polymers derived from unsaturated alcohols and amines or acyl derivatives or acetals thereof, such as polyvinyl alcohol, polyvinyl acetate, stearate, benzoate or maleate, polyvinyl butyral, polyallyl phthalate or polyallylmelamine; and also copolymers thereof with olefins mentioned in item 1.

11. Homopolymers and copolymers of cyclic ethers, such as polyalkylene glycols, polyethylene oxide, polypropylene oxide or copolymers thereof with bisglycidyl ethers.

12. Polyacetals, such as polyoxymethylene, and also polyoxymethylenes containing comonomers, for example ethylene oxide; polyacetals which have been modified with thermoplastic polyurethanes, acrylates or MBS.

13. Polyphenylene oxides and sulfides and mixtures thereof with styrene polymers or polyamides.

14. Polyurethanes derived firstly from polyethers, polyesters and polybutadienes having terminal hydroxyl groups and, secondly, from aliphatic or aromatic polyisocyanates, and also precursors thereof.

15. Polyamides and copolyamides derived from diamines and dicarboxylic acids and/or aminocarboxylic acids or the corresponding lactams, such as polyamide 4, polyamide 6, polyamide 6/6, 6/10, 6/9, 6/12 and 4/6, polyamide 11, polyamide 12. aromatic polyamides based on m-xylene, a diamine and adipic acid; polyamides prepared from hexamethylenediamine and isophthalic and/or terephthalic acid and, if appropriate, an elastomer as modifier, for example poly-2,4,4,-trimethylhexamethyleneterephthalamide or poly-m-phenyleneisophthalamide, block copolymers of the abovementioned polyamides with polyolefins, olefin copolymers, ionomers or chemically attached or grafted elastomers; or with polyethers, for example polyethylene glycol, polypropylene glycol or polytetras:ethylene glycol. Also polyamides or copolyamides modified with EPDM or ABS; and polyamides which have been condensed during processing ("RIM polyamide systems").

16. Polyureas, polyimides, polyamide-imides and polybenzimidazoles.

17. Polyesters derived from dicarboxylic acids and dialcohols and/or from hydroxycarboxylic acids or the corresponding lactones, such as polyethylene terephthalate, polybutylene terephthalate, poly-1,4,-dimethylolcyclohexane terephthalate, polyhydroxybenzoates, and block polyether-esters derived from polyethers having hydroxyl end groups; and also polyesters modified with polycarbonates or MBS.

18. Polycarbonates and polyester-carbonates

19. Polysulfones, polyether-sulfones and polyetherketones.

20. Crosslinked polymers derived firstly from aldehydes and secondly from phenols, urea or melamine, such as phenol-formaldehyde urea-formaldehyde and melamine-formaldehyde resins.

21. Drying and non-drying alkyd resins.

22. Unsaturated polyester resins derived from copolyesters of saturated and unsaturated dicarboxylic acids with polyhydric alcohols and also vinyl compounds as crosslinking agents, and also halogen-containing modifications thereof of low combustibility.

23. Crosslinkable acrylic resins derived from substituted acrylic acid esters, for example epoxy acrylates, urethane-acrylates or polyester-acrylates.

24. Alkyd resins, polyester resins and acrylate resins which have been crosslinked with melamine resins, urea resins, polyisocyanates or epoxy resins.

25. Crosslinked epoxy resins derived from polyepoxides, for example bisglycidyl ethers or cycloaliphatic diepoxides.

26. Natural polymers, such as cellulose, natural rubber, gelatin and polymer-homologously chemically modified derivatives thereof, such as cellulose acetates, propionates andbutyrates, or the cellulose ethers, such as methylcellulose, and colophony resins and derivatives.

27. Mixtures (polyblends) of the abovementioned polymers, for example PP/EPDM, polyamide/EPDM or polyamide/ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6,6 and copolymers, PA/HDPE, PA/PP and PA/PPO.

Use in lacquers is of particular importance. These can be pigmented or unpigmented lacquers and they can be cold-curing or heat curing or non-convertible. The lacquers can contain an organic solvent or they can be solvent-free or can be water-based lacquers.

The stabilizers are added to the organic materials in a concentration of 0.01 to 5% by weight, calculated on the material to be stabilized. It is also possible to use mixtures of two or more compounds of the formula I.

The compounds of the formula I can be used together with other stabilizers. These can be, for example, antioxidants or light stabilizers or co-stabilizers, for example organic phosphites or phosphonates.

The following classes of stabilizers are examples of these.

I Antioxidants 1.1. Alkylated monophenols for example 2,6-di-tert-butyl-4-methylphenol, 2-tert-butyl-4,6-dimethylphenol, 2,6-di-tert-butyl-4-ethylphenol, 2,6di-tert-butyl-4-n-butylphenol, 2,6-di-tert-butyl-4-isobutylphenol, 2,6-di-cyclopentyl-4-methylphenol, 2-(α-methylcyclohexyl)-4,6-dimethylphenol, 2,6-di-octadecyl-4-methylphenol, 2,4,6-tri-cyclohexylphenol-2,6-di-tert-butyl-4-methoxymethylphenol or 2,6-di-nonyl-4-methylphenol.

1.2. Alkylated hydroquinones, for example 2,6-di-tert-butyl-4,methoxyphenol, 2,5-di-tert-butylhydroquinone,2,5-di-tert-amylhydroquinoneor2,6-diphenyl. 4-octadecyloxyphenol.

1.3. Hydroxylated thiodiphenyl ethers, for example, 2,2'-thiobis-(6-tert-butyl-4-methylphenol), 2,2'-thiobis-(4-octylphenol), 4,4'-thiobis-(6tert-butyl-3-methylphenol) or 4,4'-thiobis-(6-tert-butyl-2-methylphenol)

1.4 Alkylidenebisphenols, for example, 2,2'-methylenebis-(6-tert-butyl-4-methylphenol), 2,2'-methylenebis-(6-tert-butyl-4-ethylphenol), 2,2-methylenebis-[4-methyl-6-(α-methylcyclohexyl)-phenol], 2,2'-methylenebis-(4-methyl-6-cyclohexylphenol), 2,2'-methylenebis-(6-nonyl-4-methylphenol), 2,2'-methylenebis-(4,6-di-tert-butylphenol), 2,2'-ethylidenebis-(4,6-di -tert-butylphenol), 2,2'-ethylidenebis-(6-tert-butyl-4-isobutylphenol), 2,2'-methylenebis-[6-(α-methylbenzyl)-4-nonylphenol, 2,2'-methylenebis-[6-(α,α-dimethylbenzyl)-4-nonylphenol], 4,4'-methylenebis-[6-(α,α-dimethylbenzyl)-4-nonylphenol], 4,4'-methylenebis-(2,6-di-tert-butylphenol), 4,4,'-methylenebis-(6-tert-butyl-2-methylphenol), 1,1-bis-(5-tert-butyl-4-hydroxy-2-methylphenyl)-butane, 2,6-bis-(3-tert-butyl-5-methyl-2-hydroxybenzyl)-4methylphenol, 1,1,3-tris-(5-tert-butyl-4-hydroxy-2-methylphenyl)-butane, 1,1-bis-(5-tert-butyl-4-hydroxy 2-methylphenyl)-3-n-dodecylmercaptobutane, ethylene glycol bis-[3,3-bis-(3'-tert-butyl-4'-hydroxyphenyl)-butyrate], bis-(3-tert-butyl-4-hydroxy-5-methylphenyl)-dicyclopentadiene or bis-[2-(3'-tert-butyl-2'-hydroxy-5'-methyl-benzyl)-6-tert-butyl-4-methyl-phenyl]terephthalate.

1.5. Benzyl compounds, for example,1,3,5-tris-(3,5-di-tert-butyl-4-hydroxybenzyl)-2,4,6-trimethylbenzene, bis-(3,5-di-tert-butyl-4-hydroxy-benzyl)sulfide,isooctyl 3,5-di-tert-butyl-4-hydroxybenzylmercaptoacetate, bis-(4-tert-butyl-3-hydroxy-2,6-dimethylbenzyl)dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, dioctadecyl 3,5-di-tert-butyl-4-hydroxybenzylphosphonate, the Ca salt of monoethyl 3,5-di-tert-butyl-4-hydroxybenzylphosphonate or1,3,5-tris-(3,5 dicyclohexyl-4-hydroxybenzyl) isocyanurate.

1.6. Acylaminophenols, for example, 4-hydroxylauranilide, 4-hydroxystearanilide, 2,4-bis-(octylmercapto)-6-(3,5-di-tert-butyl-4-hydroxyanilino)-s-triazine or octyl N-(3,5-di-tert-butyl-4-hydroxyphenyl)-carbamate.

1.7. Esters of β-(3 5-di-tert-butyl-4-hydroxyphenyl)-propionic acid with monohydric or polyhydric alcohols, for example methanol, octadecanol, 1,6-hexanediol, neopentyl glycol, thiodiethylene glycol, diethylene glycol, triethylene glycol, pentaerythritol, tris-(hydroxyethyl) isocyanurate or N,N'-bis-(hydroxyethyl)-oxamide.

1.8. Esters of β-(5-tert-butyl-.4-hydroxy-3-methylphenyl)-propionic acid with monohydric or polyhydric alcohols, for example methanol, octadecanol, 1,6-hexanediol, neopentyl glycol, thiodiethylcne glycol, diethylene glycol, triethylene glycol, pentaerythritol, tris-(hydroxyethyl) isocyanurate or N,N'-bis-(hydroxyethyl)-oxamide.

1.9. Esters of β-(3 5-dicyclohexyl-4-hydroxyphenyl)-propionic acid with monohydric or polyhydric alcohols, for example methanol, octadecanol, 1,6-hexanediol, neopentyl glycol, thiodiethylene glycol, diethylene glycol, triethylene glycol, pentaerythritol, tris- (hydroxyethyl) isocyanurate or N,N'-bis-(hydroxyethyl)-oxamide 1.10. Amides of β-(3,5-di-tert-butyl-4 hydroxyphenyl)-propionic acid, for example, N,N'-bis-(3,5-di-tert-butyl-4-hydroxyphenylpropionyl)-hexamethylenediamine, N,N'-bis-(3,5-di-tert-butyl-4-hydroxyphenylpropionyl)-trimethylenediamine or N,N'-bis-(3,5-di-tert-butyl-4-hydroxyphenylpropionyl)-hydrazine.

2. UV Absorbers and light stabilizers 2.1. 2-(2'-Hydroxyphenyl)-henzotriazoles, for example, the 5'-methyl-, 3',5'-di-tert-butyl-, 5'-tert-butyl-, 5'-(1,1,3,3-tetramethylbutyl)-, 5-chloro-3', 5'-di-tert-butyl-, 5-chloro-3'-tert-butyl-5'-methyl-, 3'-sec-butyl-5'-tert-butyl, 4'-octoxy-, 3', 5'-di-tert-amyl- or 3', 5'-bis-(α,α-dimethylbenzyl).derivative.

2.2. 2-Hydroxybenzophenones, for example, the 4-hydroxy-, 4-methoxy-, 4-octoxy-, 4-decyloxy-, 4-dodecyloxy-, 4-benzyloxy-, 4,2,4'-trihydroxy, or 2'-hydroxy-4,4'-dimethoxy-derivative.

2.3. Esters of substituted or unsubstituted benzoic acids, for example, 4-tert-butylphenyl salicylate, phenyl salicylate, octylphenyl salicylate, dibenzoylresorcinol, bis-(4-tert-butylbenzoyl) resorcinol, benzoylresorcinol, 2,4-di-tert-butylphenyl 3,5-di-tert-butyl-4-hydroxybenzoate or hexadecyl 3,5-di-tert-butyl-4-hydroxybenzoate.

2.4. Acrylates, for example, ethyl or isooctyl α-cyano-β,β-diphenylacrylate, methyl α-carbomethoxycinnamate, methyl or butyl α-cyano-β-methyl-p-methoxycinnamate, methyl α-carbomethoxy-p-methoxycinnamate or N-(β-carbomethoxy-β-cyanovinyl)-2-methylindoline.

2.5. Nickel compounds, for example, nickel complexes of 2,2'-thiobis-[4-(1,1,3,3-tetramethylbutyl)-phenol], such as the 1:1 or the 1:2 complex, if appropriate containing additional ligands, such as n-butylamine, triethanolamine or N-cyclohexyldiethanolamine, nickel dibutyldithiocarbamate, nickel salts of monoalkyl esters of 4-hydroxy-3,5-di-tert-butylbenzylphosphonic acid, such as the methyl or ethyl ester, nickel complexes of ketoximes, such as 2-hydroxy-4-methylphenyl undecyl ketone oxime, or nickel complexes of 1-phenyl-4-lauroyl-5-hydroxypyrazole, if appropriate containing additional ligands.

2.6. Sterically hindered amines, for example, bis-(2,2,6,6-tetramethylpiperidyl) sebacate, bis-(1,2,2,6,6-pentamethylpiperidyl) sebacate, bis-(1,2,2,6,6-pentamethylpiperidyl)n-butyl-3,5-di-tert-butyl-4hydroxybenzyl-malonate, the condensation product formed from 1-hydroxyethyl-2,2,6,6,-tetramethyl-4-hydroxypiperidine and succinic acid, the condensation product formed from N,N'-bis-(2,2,6,6-tetramethyl-4-piperidyl)-hexamethylenediamine and 4-tert-octylamino-2,6-dichloro-1,3,5-s-triazine, tris-(2,2,6,6-tetramethyl-4-piperidyl) nitrilotriacetate, tetrakis-(2,2,6,6-tetramethyl-4-piperidyl) 1,2,3,4-butanetetraoate or 1,1'(1,2-ethanediyl)-bis-(3,3,5,5-tetramethylpiperazinone).

2.7. Oxamides, for example, 4,4'-di-octyloxy-oxanilide, 2,2'-dioctyloxy-5,5'-di-tert-butyl-oxanilide, 2,2'-didodecyloxy-5,5'-di-tert-butyl-oxanilide, 2-ethoxy-2'-ethyloxanilide, N,N'-bis-(3-dimethylaminopropyl).oxamide, 2-ethoxy-5-tert-butyl-2'-ethyloxanilide and a mixture thereof with 2.ethoxy-2'-ethyl-5,4'-di-tert-butyl-oxanilide or mixtures of α-methoxy-substituted and p-methoxy-substituted oxanilides and of α-ethoxy-disubstituted and p-ethoxy-disubstituted oxanilides.

3. Metal deactivators, for example N,N'-diphenyloxamide, N-salicylal-N'-salicyloylhydrazine, N,N'-bis-(salicyloyl)-hydrazine, N,N'-bis-(3,5-di-tert-butyl-4-hydroxyphenylpropionyl)-hydrazine, 3-salicyloylamino-1,2,4-triazole or bis-(benzylidene)-oxalic acid dihydrazide.

4. Phosphites and phosphonites, for example triphenyl phosphite, diphenyl alkyl phosphites, phenyl dialkyl phosphites, tris-(nonylphenyl) phosphite, trilauryl phosphite, trioctadecyl phosphite, distearyl pentaerythrityl diphosphite, tris-(2,4-di-tert-butylphenyl) phosphite, diisodecyl pentaerythrityl diphosphite, bis-(2,4-di-tert-butylphenyl) pentaerythrityl diphosphite, tristearyl sorbityl triphosphite, tetrakis.(2,4-di tert-butylphenyl) 4,4'-biphenylenediphosphonite or 3,9-bis-(2,4-di-tert-butylphenoxy)-2,4,8,10-tetraoxa-3,9-diphosphaspiro[5,5undecane.

5. Compounds which destroy peroxides for example esters of β-thiodipropionic acid, for example the lauryl, stearyl, myristyl or tridecyl ester, mercaptobenzimidazole, the zinc salt of 2-mercaptobenzimidazole, zinc dibutyldithiocarbamate, dioctadecyl disulfide or pentaerythrityl tetrakis(β-dodecylmercapto)-propionate.

6. Polyamide stabilizers, for example copper salts in combination with iodides and/or phosphorus compounds and salts of divalent manganese.

7. Basic co-stabilizers for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example Ca stearate, Zn stearate, Mg stearate, Na ricinoleate or K palmitate, antimony pyrocatecholate or tin pyrocatecholate.

If plastics are to be stabilized, examples of further additives which can be used are antistatic agents, plasticizers, slip agents, fire-retarding agents, blowing agents, metal deactivators, fillers, reinforcing agents or pigments. If lacquers are to be stabilized, examples of further additives which can be used are flow control agents, curing accelerators, thickening agents or adhesion promoters. If photographic materials are to be stabilized, examples of further additives which can be used are colour cast inhibitors, hydroquinone compounds or solvents.

The invention also relates, therefore, to organic materials containing, as the stabilizer, at least one compound of the formula I.

The organic materials are preferably plastics, lacquers or photographic emulsions. The materials thus stabilized contain 0.01 to 5% by weight of the stabilizer of the formula I.

The following examples describe the invention in greater detail without limiting the invention to the examples. In these examples parts are parts by weight and % are % by weight, unless stated otherwise.

EXAMPLE 1

Preparation of the benzotriazoles by diazotization coupling and reduction (a) Diazotization 0.17 mol of finely powdered 2-nitroaniline is introduced into 50 ml of 37% hydrochloric acid at room temperature. The yellow suspension warms up to 30–35° C. It is cooled to 0.5° C. with ice. An approx. 30% aqueous solution of this temperature in the course of 50 minutes. A brown solution is formed and is stirred for one hour to complete the reaction. After 1 g of active charcoal has been added, the solution is filtered through silica. Excess nitrous acid can be removed by means of sulfamic acid beforehand. Filtration gives a pale yellow, clear solution, which is used further in (b).

(b) Coupling 0.15 mol of 2-(1,1-dimethyl-4-methoxycarbonylbutyl)-4-methylphenol, dissolved in a solution of 0.25 mol of sodium hydroxide in 100 ml of water and a little isopropanol, is heated to 70–80° C. and stirred for approx. 30 minutes. In the course of this the ester group is saponified and the phenol dissolves. The solution is cooled to 0–5° C. and the above diazonirs salt solution is added dropwise. The time of dropwise addition is approx. 1 hour. The pH of the solution is kept at 11–12. Slight foaming is suppressed by adding 1 ml of n-octanol. After the dropwise addition a dark violet solution of azo dye is obtained This is used further as such.

(c) Reduction

A further 1.5 mol of sodium hydroxide in 200 ml of water and 50 ml of ethylcellulose are added to the dye solution, and the mixture is heated to 80° C. 0.2 mol of hydrazine hydrate is added dropwise to the dark violet solution at this temperature in the course of 20 minutes. The reaction solution turns dark brown and there is a distinct evolution of nitrogen. After being stirred for 2 hours at 80° C. to complete the reaction, the mixture is cooled to 40–50° C. and 0.3 mol of zinc dust is introduced in portions. An exothermic reaction takes place and the solution turns a grey-green colour. It is stirred for approx. 2–3 hours at 70–80° C. to complete the reaction and is then filtered while hot through silica. This gives a clear, brown filtrate, which is acidified to Congo with concentrated hydrochloric acid (37%), with cooling. The brown crude product which is precipitated is purified by recrystallization or by column chromotography (silica gel) or is processed further in the crude form (see d).

(d) Esterification 0.15 mol of the crude benzotriazolecarboxylic acid in 250 ml of methanol is heated to reflux temperature, and 2 ml of concentrated sulfuric acid are added dropwise at this temperature ($\approx 65°$ C.). After a reflux time of approx. 3 hours the thin layer chromatogram no longer indicates benzotriazolecarboxylic acid. Evaporating the methanol solution gives the crude 2-[2-hydroxy-3-(1.1-dimethyl-4-methoxycarbonylbutyl)-5-methyl]-benzotriazole as a brownish product. The product can be recrystallized from methanol or from petroleum ether (80–100° C.). Melting point 88–90° C. (Compound No. 1).

The compounds listed in Table 1 can be prepared analogously from the α-nitrophenyl diazonium salt and the corresponding phenols.

TABLE 1

| Compound No. | Formula | Physical properties, analysis |
|---|---|---|
| 2 | [benzotriazole structure with HO, C(CH$_3$)$_2$—CH$_2$CH$_2$CH$_2$COOCH$_3$ and C(CH$_3$)$_2$—CH$_2$CH$_2$CH$_2$COOCH$_3$ substituents] | Oil<br>N = 8.43%,<br>calc. 8.48% |
| 3 | [benzotriazole structure with HO, C(CH$_3$)$_2$—CH$_2$CH$_2$CH$_2$COOCH$_3$ and C(CH$_3$)$_2$—C$_2$H$_5$ substituents] | m.p. 77–80° C.<br>(from Methanol) |
| 4 | [benzotriazole structure with HO, C(CH$_3$)$_2$—CH$_2$CH$_2$CH$_2$COOCH$_3$ and CH(CH$_3$)—C$_2$H$_5$ substituents] | Oil<br>N = 10.14%,<br>calc. 10.26% |

TABLE 1-continued
| Compound No. | Formula | Physical properties, analysis |
|---|---|---|
| 5 | 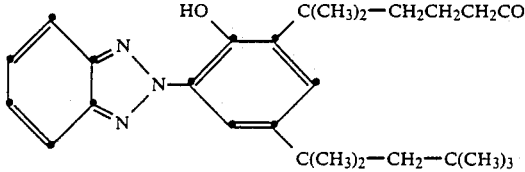 | Oil<br>N = 8.78%,<br>calc. 9.02% |
| 6 | 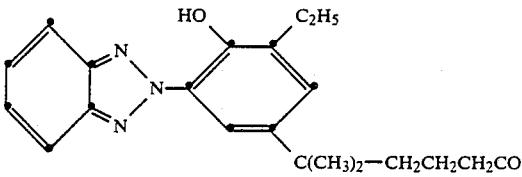 | m.p. 51-53° C.<br>(from Methanol) |
| 7 | 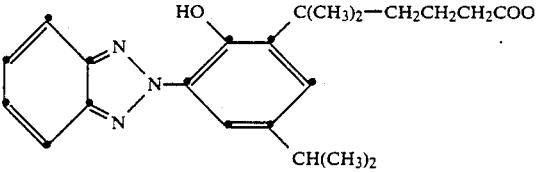 | Oil<br>N = 10.49%,<br>calc. 10.62% |
| 8 | 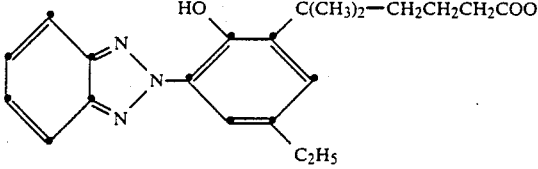 | m.p. 81-82° C.<br>(from Methanol) |
| 9 | 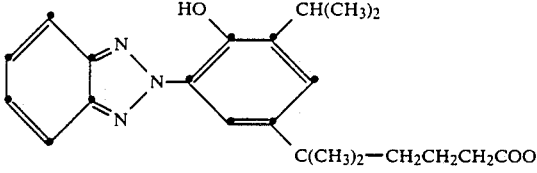 | Oil<br>N = 10.4%,<br>calc. 10.6% |
| 10 | 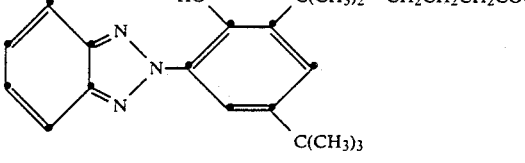 | Oil |
| 11 | 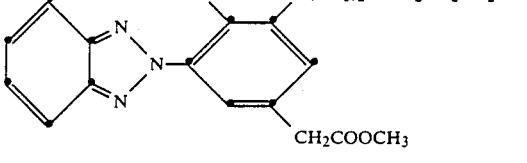 | Oil<br>N = 9.50%,<br>calc. 9.88% |
| 12 | 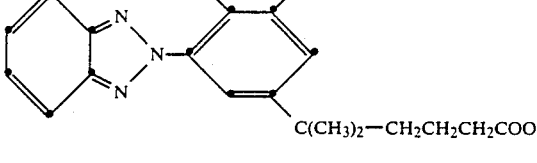 | m.p. 92-93° C.<br>(from Methanol) |

TABLE 1-continued

| Compound No. | Formula | Physical properties, analysis |
|---|---|---|
| 13 | Benzotriazolyl-phenol with HO, C(CH$_3$)$_2$—CH$_2$CH$_2$CH$_2$COOCH$_3$, and CH$_2$CH$_2$COOCH$_3$ substituents | m.p. 82–84° C. (from Methanol) |
| 14 | Benzotriazolyl-phenol with HO, C(CH$_3$)$_2$—CH$_2$CH$_2$CH(CH$_3$)CH$_2$CH$_2$OH, and CH(CH$_3$)$_2$ substituents | Oil  N = 9.65% calc. 10.26% |
| 15 | Benzotriazolyl-phenol with HO, C(CH$_3$)$_3$, and C(CH$_3$)$_2$—CH$_2$CH$_2$CH$_2$COOCH$_3$ substituents | m.p. 79–81° C. (from Methanol) |
| 16 | Benzotriazolyl-phenol with HO, CH(CH$_3$)—C$_2$H$_5$, and C(CH$_3$)$_2$—CH$_2$CH$_2$CH$_2$COOCH$_3$ substituents | Oil  N = 10.33%, calc. 10.26% |
| 17 | Benzotriazolyl-phenol with HO and C(CH$_3$)$_2$—CH$_2$CH$_2$CH$_2$COOCH$_3$ substituents | m.p. 66–68° C. (from Methanol) |
| 18 | Benzotriazolyl-phenol with HO, C$_2$H$_5$, and C(CH$_3$)$_2$—(CH$_2$)$_3$—COOCH$_2$CH(CH$_3$)C$_3$H$_7$ substituents | Oil  N = 9.30% calc. 9.30% |
| 19 | Benzotriazolyl-phenol with HO, C(CH$_3$)$_2$—(CH$_2$)$_3$—COOCH$_2$CH(CH$_3$)C$_3$H$_7$, and C$_2$H$_5$ substituents | Oil  N = 9.37% calc. 9.30% |
| 20 | Benzotriazolyl-phenol with HO, C(CH$_3$)$_2$—(CH$_2$)$_3$—COOCH$_2$CH(CH$_3$)C$_3$H$_7$, and C(CH$_3$)$_3$ substituents | Oil  N = 8.72% 8.76% |

TABLE 1-continued

| Compound No. | Formula | Physical properties, analysis |
|---|---|---|
| 21 | 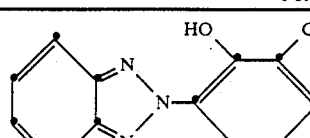<br>C(CH₃)₂—(CH₂)₃—COOCH₂CHC₃H₇ (with CH₃ branch) | Oil<br>N = 8.77%<br>calc. 8.76% |
| 22 | 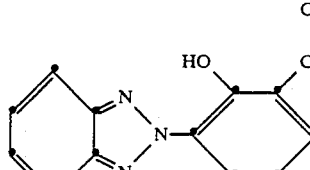<br>C(CH₃)₂—(CH₂)₃—COOCH₂CHC₃H₇ (with CH₃ branch) | Oil<br>N = 9.03%<br>calc. 8.58% |

EXAMPLE 2

Transesterification of the benzotriazoles

A mixture of 18.4 g of 2-[2-hydroxy-3-(1,1-dimethyl-4-methoxycarbonylbutyl)-5-methyl)-phenyl]-benzotriazole (Compound No. 1), 3,4 g of n-octanol, 3.4 g of 2-ethylhexanol and 0.12 g of dibutyltin oxide is heated to 150° C. in a 250 ml sulfonation flask equipped with stirrer, a distillation head, a thermometer and nitrogen flushing. Toluene is added dropwise at this temperature and is distilled off continuously, together with the methanol formed. After three hours thin-layer chromatogram shows that no more methyl ester is present in the reaction mixture. After cooling, the reaction mixture is dissolved in methylene chloride, and the solution is filtered through silica and evaporated in vacuo. This gives a yellow oil (Compound No. 23), which is a 1:1 mixture of 2-[2-hydroxy-3-(1,1-dimethyl-4-n-octyloxycarbonyl-butyl)-5-methyl)-phenyl]-benzotriazole and 2-[2-hydroxy 3-(1,1-dimethyl-4-8 2-ethylhexyloxy]carbonyl-5-methyl)-phenyl]-benzotriazole.

Analysis Found C=72.33 H=8.26 N=9.27% Calculated C=72.13 H=8.44 N=9.02%

The compounds listed in Table 2 are prepared analogously.

TABLE 2

| Compound No. | Formula | Physical properties, analysis |
|---|---|---|
| 24 | 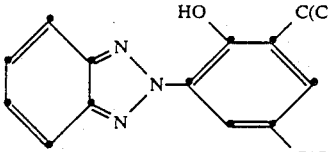<br>prepared from Compound No. 2 | Oil<br>found 7.07% N<br>calc. 6.91% N |
| 25 | 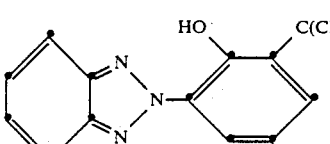<br>prepared from Compound No. 10 | Oil<br>found 7.95% N<br>calc. 8.28% N |
| 26 | 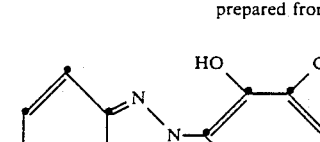<br>prepared from Compound No. 10 | Oil<br>found 8.92% N<br>calc. 9.02% N |

TABLE 2-continued

| Compound No. | Formula | Physical properties, analysis |
|---|---|---|
| 27 | from Compound No. 2 and polyethylene glycol 300 with substituents HO, C(CH$_3$)$_2$—(CH$_2$)$_3$—COO(CH$_2$CH$_2$O)$_{6-7}$H (×2) on benzotriazolyl-phenyl | Oil<br>N = 4.51%<br>calc. 4.22% |
| 28 | from Compound No. 2 and polyethylene glycol 350 monomethyl ether; substituents HO, C(CH$_3$)$_2$—(CH$_2$)$_3$—COO(CH$_2$CH$_2$O)$_{7-8}$CH$_3$ (×2) | Oil<br>N = 4.00%<br>calc. 4.10% |
| 29 | from Compound No. 21 and 1,6-hexanediol; substituents HO, C(CH$_3$)C$_2$H$_5$, C(CH$_3$)$_2$—(CH$_2$)$_3$—COOCH$_2$CH$_2$CH$_2$—]$_2$ | Resin<br>N = 9.66%<br>calc. 9.62% |
| 30 | from Compound No. 9 and polyethylene glycol 300; substituents HO, C(CH$_3$)$_2$, C(CH$_3$)$_2$—(CH$_2$)$_3$—COO(CH$_2$CH$_2$O)$_{6-7}$H | Oil<br>N = 6.44%<br>calc. 6.09% |

EXAMPLE 3

Esterification of the benzotriazolecarboxylic acids with epoxides 0.05 mol of 2-[2-hydroxy-3-ethyl-5-(1,1-dimethyl-4-carboxybutyl)-phenyl]-benzotriazole is dissolved in 100 ml of toluene. The solution is heated to 80° C. and 0.055 mol of butyl glycidyl ether is added, together with 0.005 mol of uimethylbenzylamine as catalyst After being stirred for 12 hours at 80° C. the solution is evaporated in vacuo. The oily residue is chromatographed over silica gel. The compound

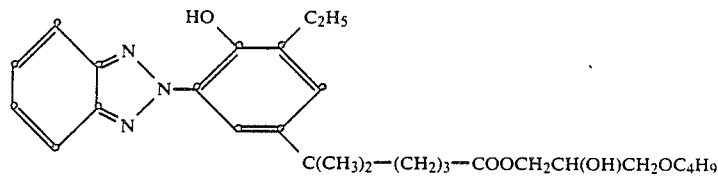

is obtained in the form of a colourless resin (Compound No. 31). Analysis: N calculated 8.51% found 8.44%

The compound

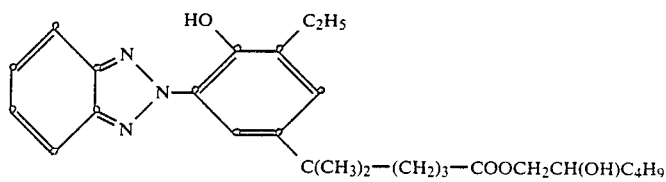

is obtained analogously in the form of a yellowish oil (Compound No. 32), using butyloxirane (hex-1-ene oxide).

EXAMPLE 4

Esterification and amidation via the carboxylic acid chloride (a) Preparation of the carboxylic acid chloride 0.1 mol of 2-[2-hydroxy-3-ethyl-5 (1,1-dimethyl-4-carboxybutyl)-phenyl]-benzotriazole is dispersed in 200 ml of hexane. After 0.5 ml of dimethylformamide has been added, 0.12 mol of thionylchloride is added dropwise slowly, with stirring. A vigorous evolution of gas (an $HCl/SO_2$ mixture) is set up and the temperature rises to 35° C. When the dropwise addition is complete the mixture is heated slowly to reflux temperature. A clear, brown solution is formed. The reaction is complete after 3 hours. The solution is filtered while warm and is evaporated in vacuo. This leaves a yellow oil, which is used further without purification.

(b) Reaction of the carboxylic acid chloride 0.065 mol of diisooctylamine and 0.15 mol of triethylamine are dissolved in 50 ml of toluene. The solution is cooled to 0-5° C. under argon. A solution of 0.064 mol of the acid chloride described under (a) in 50 ml of toluene is added dropwise at this temperature with stirring. This produces a precipitate of triethylamine hydrochloride. After the dropwise addition the suspension is stirred for a further 2 hours and filtered. The filtrate is washed with dilute hydrochloric acid and water, dried over $Na_2SO_4$ and evaporated. The dark yellow oily residue is purified by chromatography over a silica gel column. This gives 2-[2-hydroxy-3-ethyl-5-(1,1-dimethyl-4-(diisooctylaminocarbonyl)-butyl)-phenyl]-benzotriazole (Compound No. 33) in the form of a yellowish resin.

Analysis: N calculated 9.48% found 9.38%

The compounds listed in Table 3 are obtained analogously.

EXAMPLE 5

Stabilization of a magenta layer

A gelatin layer containing silver bromide and a magenta coupler is first applied to a base material coated with polyethylene, and a gelatin layer containing the UV absorber according to invention is then applied (covering layer).

The gelatin layers consist of the following components (per $m^2$ of base material):

| Component | AgBr layer | Covering layer |
|---|---|---|
| Gelatin | 5.15 g | 1.3 g |
| Curing agent | 300 mg | 80 mg |
| Wetting agent | 85 mg | 100 mg |
| Silver bromide | 520 mg | — |
| Tricresylphosphate | 164 mg | 510 mg |
| Magenta coupler | 329 mg | — |
| UV absorber | — | 1.1 mmol |

The magenta coupler has the following structure:

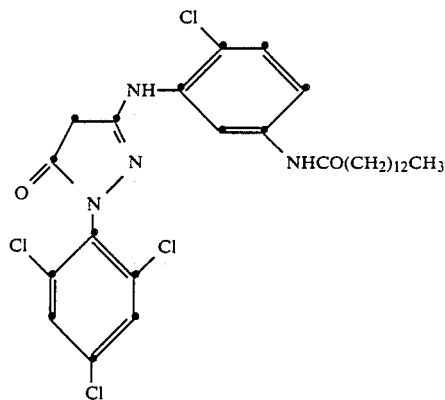

TABLE 3

| Compound No. | Formula | Physical properties, analysis |
|---|---|---|
| 34 | [benzotriazole with HO, $C(CH_3)_3$, and $C(CH_3)_2$—$(CH_2)_3$—$CON(i-C_8H_{17})_2$ substituents] | Resin N = 8.99% calc. 9.05% |
| 35 | [benzotriazole with HO, $C_2H_5$, and $C(CH_3)_2$—$(CH_2)_3$—$CON$—$(CH_2)_3$ with $C_3H_7$-i, dimer]$_2$ | Resin N = 12.44% calc. 12.46% |
| 36 | [benzotriazole with HO, $C_2H_5$, and $C(CH_3)_2$—$(CH_2)_3$—$COOCH_2CH_2P(O)(OCH_3)_2$] | Resin N = 8.57% calc. 8.34% |

2.4-Dichloro-6-hydroxytriazine is used as the curing agent. The sodium salt of diisobutylnaphthalenesulfonic acid is used as the wetting agent.

A step wedge having a density difference of 0.15 logE per step is exposed to light on top of each of the 5 samples thus obtained, and the procedure specified in the instructions of the manufacturer in the Kodak process E+2 for negative colour paper is then followed.

To determine the yellowing, the diffuse reflectance density in the blue is then measured. The wedge is then exposed to a total of 15 kJ/cm² in an Atlas exposure instrument, the diffuse reflectance density (in the blue) is measured again and the increase in yellow dye is calculated. The results with various UV absorbers are shown in Table 4.

TABLE 4

| UV absorber | Increase in yellow ($\Delta D_{min}{}^b$) |
| --- | --- |
| None | 0.35 |
| Compound No. 2 | 0.17 |
| Compound No. 18 | 0.17 |
| Compound No. 19 | 0.16 |

EXAMPLE 6

Stabilization of a yellow layer

The procedure of Example 5 is repeated, using the yellow coupler A of the following formula:

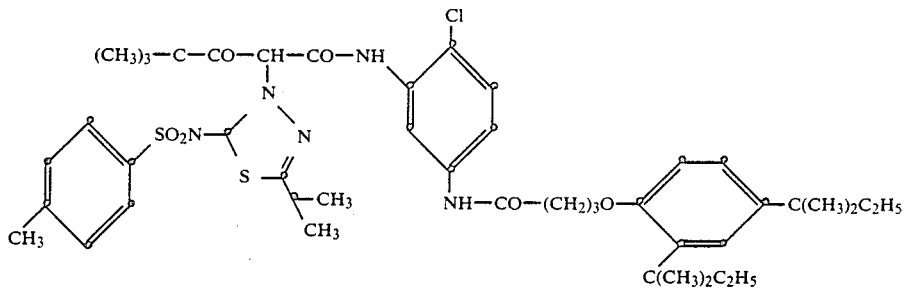

The gelatin layers have the following composition (per m²):

| Component | AgBr layer | Covering layer |
| --- | --- | --- |
| Gelatin | 5.15 g | 1.3 g |
| Curing agent | 300 mg | 80 mg |
| Wetting agent | 340 mg | 100 mg |
| Silver bromide | 520 mg | — |
| Tricresylphosphate | 309 mg | 510 mg |
| Yellow coupler A | 927 mg | — |
| UV absorber | — | 1.1 mmol |

After exposure and processing as described in Example 5, the diffuse reflectance density in the blue is measured for the yellow step at a density of the wedge between 0.9 and 1.1. The wedge is then exposed at a total of kJ/cm² in an Atlas exposure instrument and the diffuse reflectance density is determined again.

The percentage losses in density listed in Table 5 can be calculated on the basis of the values thus obtained.

TABLE 5

| UV absorber | Loss in density |
| --- | --- |
| None | 33% |
| Compound No. 2 | 16% |
| Compound No. 18 | 17% |
| Compound No. 19 | 15% |

EXAMPLE 7

Stabilization of a cyan layer

The procedure of Example 5 is repeated, but using the cyan coupler of the following formula:

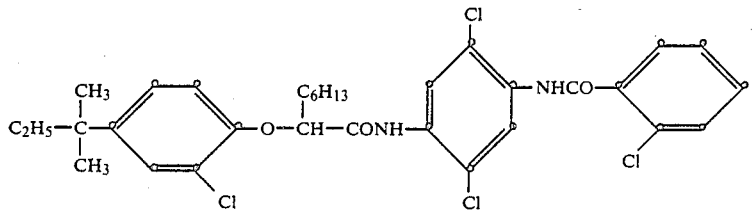

The gelatin layers have the following composition (per m²)

| Component | AgBr layer | Covering layer |
| --- | --- | --- |
| Gelatin | 5.15 g | 1.3 g |
| Curing agent | 300 mg | 80 mg |
| Wetting agent | 170 mg | 100 mg |
| Silver bromide | 260 mg | — |
| Tricresylphosphate | 220 mg | 510 mg |
| Cyan coupler | 331 mg | — |
| UV absorber | — | 1.1 mmol |

After exposure and processing as described in Example 5, the diffuse reflectance density in the red is determined for the cyan step at a density of the wedge between 0.9 and 1.1. The wedge is then exposed at a total of 15 kJ/cm² in an Atlas exposure instrument and the diffuse reflectance density is determined again.

The percentage losses in density listed in Table 6 can be calculated on the basis of the values thus obtained.

TABLE 6

| UV absorber | Loss in density |
| --- | --- |
| None | 21% |
| Compound No. 2 | 15% |
| Compound No. 18 | 15% |

TABLE 6-continued

| UV absorber | Loss in density |
|---|---|
| Compound No. 19 | 14% |

EXAMPLE 8

Stabilization of a yellow layer

The procedure of Example 5 is repeated, but using the yellow coupler B of the following formula:

[Structure of yellow coupler B]

The gelatin layers have the following composition (per m$^2$)

| Component | AgBr layer | Covering layer |
|---|---|---|
| Gelatin | 5.15 g | 1.3 g |
| Curing agent | 300 mg | 80 mg |
| Wetting agent (anionic) | 340 mg | 100 mg |
| Silver bromide | 520 mg | — |
| Tricresylphosphate | 214 mg | 510 mg |
| Yellow coupler B | 641 mg | — |
| UV absorber | — | 1.1 mmol |

After exposure and processing as described in Example 5, the diffuse reflectance density in the blue is determined for the yellow step at a density of the wedge between 0.9 and 1.1. The wedge is then exposed at a total of 15 kJ/cm$^2$ in an Atlas exposure instrument and the diffuse reflectance density is determined again.

The percentage losses in density listed in Table 7 can be calculated on the basis of the values thus obtained.

TABLE 7

| UV absorber | Loss in density |
|---|---|
| None | 59% |
| Compound No. 2 | 31% |
| Compound No. 18 | 33% |
| Compound No. 19 | 31% |

What is claimed is:

1. A compound of formula I $$\text{[Structure I with OH, R}^1\text{, R}^2\text{, R}^3\text{ substituents on benzotriazole]}$$

in which R$^1$ is located in the ortho-position or para-position relative to the OH group and is a group of formula IIa $$-\underset{\underset{CH_3}{|}}{\overset{\overset{CH_3}{|}}{C}}-(CH_2)_3-COOR^6 \quad \text{IIa}$$

in which R$^6$ is C$_5$–C$_{18}$-alkyl which is unsubstituted or substituted by —OH, C$_3$–C$_{30}$-alkyl or C$_3$–C$_{30}$-hydroxyalkyl each of which is interrupted by one or more —O— groups, or is C$_5$–C$_{12}$-cycloalkyl, C$_2$–C$_{18}$-alkenyl, C$_7$–C$_{15}$-aralkyl, glycidyl or furfuryl, R$^2$ is C$_1$–C$_{12}$-alkyl, cyclohexyl or a group of formula IIa, or a group of formula IV $$-C_pH_{2p}-COOR^6 \quad (IV)$$

in which p is 1 or 2, and

R$^3$ is hydrogen or chlorine.

2. The compound according to claim 1 wherein formula I, R$^1$ and R$^2$ are in the ortho-and para-positions relative to the OH group and are each of formula IIa, R$^6$ is methyl and R$^3$ is hydrogen.

3. The compound according to claim 1 where in formula I, R$^1$ is in the para-position relative to the OH group and is a group of formula IIa, R$^6$ is 2-methylpentyl, R$^2$ is in the ortho-position relative to the OH group and is ethyl, and R$^3$ is hydrogen.

4. The compound according to claim 1 where in formula I, R$^1$ is in the ortho-position relative to the OH group and is a group of formula IIa, R$^6$ is 2-methylpentyl, R$^2$ is in the para-position relative to the OH group and is ethyl, and R$^3$ is hydrogen.

* * * * *